US012585014B2

(12) United States Patent
D'Hooge et al.

(10) Patent No.: US 12,585,014 B2
(45) Date of Patent: Mar. 24, 2026

(54) FLEXIBLE ULTRASOUND TRANSDUCER

(71) Applicant: KATHOLIEKE UNIVERSITEIT LEUVEN, Leuven (BE)

(72) Inventors: Jan D'Hooge, Mechelen (BE); Marcus Ingram, Rotselaar (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

(21) Appl. No.: 18/549,672

(22) PCT Filed: Mar. 9, 2022

(86) PCT No.: PCT/EP2022/056093
§ 371 (c)(1),
(2) Date: Sep. 8, 2023

(87) PCT Pub. No.: WO2022/189534
PCT Pub. Date: Sep. 15, 2022

(65) Prior Publication Data
US 2024/0159897 A1      May 16, 2024

(30) Foreign Application Priority Data

Mar. 9, 2021    (EP) ..................................... 21161574
Dec. 2, 2021    (WO) ................. PCT/EP2021/083992

(51) Int. Cl.
*G01S 15/89*      (2006.01)
*A61B 8/00*      (2006.01)
*G01S 7/52*      (2006.01)

(52) U.S. Cl.
CPC ........ *G01S 15/8936* (2013.01); *A61B 8/4488* (2013.01); *G01S 7/52036* (2013.01); *G01S 7/5205* (2013.01); *G01S 15/8918* (2013.01)

(58) Field of Classification Search
CPC ............. G01S 15/8936; G01S 15/8918; G01S 7/52036; G01S 7/5205; A61B 8/4488
See application file for complete search history.

(56) References Cited

U.S. PATENT DOCUMENTS 5,269,307 A * 12/1993 Fife ..................... G01S 15/8918
                                                                  600/447
5,348,013 A * 9/1994 Kanda ................. G01S 7/52026
                                                                  600/443

(Continued)

OTHER PUBLICATIONS

Noda, T. et al., "Self-Shape Estimation Algorithm for Flexible Ultrasonic Transducer Array Probe by Minimizing Entropy of Reconstructed Image", Oct. 6, 2019, 2019 IEEE International Ultrasonics Symposium (IUS), pp. 131-134.

(Continued)

*Primary Examiner* — Dixomara Vargas
(74) *Attorney, Agent, or Firm* — Workman Nydegger

(57) ABSTRACT

An actual shape estimation method for a flexible ultrasound device and to an ultrasound imaging system includes an actual shape estimation module. The module, when executed, performs the steps of the method, including determining a series of shape metrics based on a predetermined series of assumed shapes of the flexible ultrasound device, and selecting an optimal shape metric, corresponding with the smallest or largest shape metric—depending on how the shape metric is defined, of the determined series of shape metrics, wherein the assumed shape of the predetermined series of assumed shapes of the flexible ultrasound device corresponding to the optimal shape metric provides an estimation of the actual shape of the flexible ultrasound device.

15 Claims, 14 Drawing Sheets

(56) References Cited

U.S. PATENT DOCUMENTS

| | | | | |
|---|---|---|---|---|
| 2004/0122323 A1* | 6/2004 | Vortman | .................. | A61N 7/02 |
| | | | | 600/459 |
| 2012/0330197 A1* | 12/2012 | Makin | .................. | A61B 8/4281 |
| | | | | 601/3 |
| 2012/0330223 A1* | 12/2012 | Makin | .................. | A61B 8/4281 |
| | | | | 606/27 |
| 2018/0043473 A1* | 2/2018 | Helvajian | ................ | G01H 9/00 |
| 2022/0001157 A1* | 1/2022 | Kim | ........................... | B25J 9/12 |
| 2022/0126120 A1* | 4/2022 | Zachar | ................ | A61B 8/5207 |
| 2022/0233890 A1* | 7/2022 | Hynynen | ............. | A61B 8/4477 |
| 2022/0249059 A1* | 8/2022 | Hsieh | .................. | A61B 8/0841 |
| 2023/0024998 A1* | 1/2023 | Greenberg | .......... | A61B 8/4488 |

OTHER PUBLICATIONS

Cruza, Jorge F. et al., "Real Time Autofocusing Hardware for Ultrasonic Imaging with Interfaces", 2015 IEEE International Ultrasonics Symposium Proceedings (IUS). IEEE, Oct. 1, 2015, p. 1-4.
Hunter, Alan J., et al., "Autofocusing Ultrasonic Imagery for Non-Destructive Testing and Evaluation of Specimens with Complicated Geometries", NDT & E International, vol. 43, Sep. 16, 2009, 78-85.
International Search Report from PCT/EP2021/083992, Feb. 10, 2022.
International Search Report from PCT/EP2022/056093, Jul. 8, 2022.

* cited by examiner

101

S1 — Defining a series of assumed shapes of flexible ultrasound device

S2 — Determining a series of shape metrics based on defined series of assumed shapes S3 — Selecting optimal shape metric of determined series of shape metrics

102

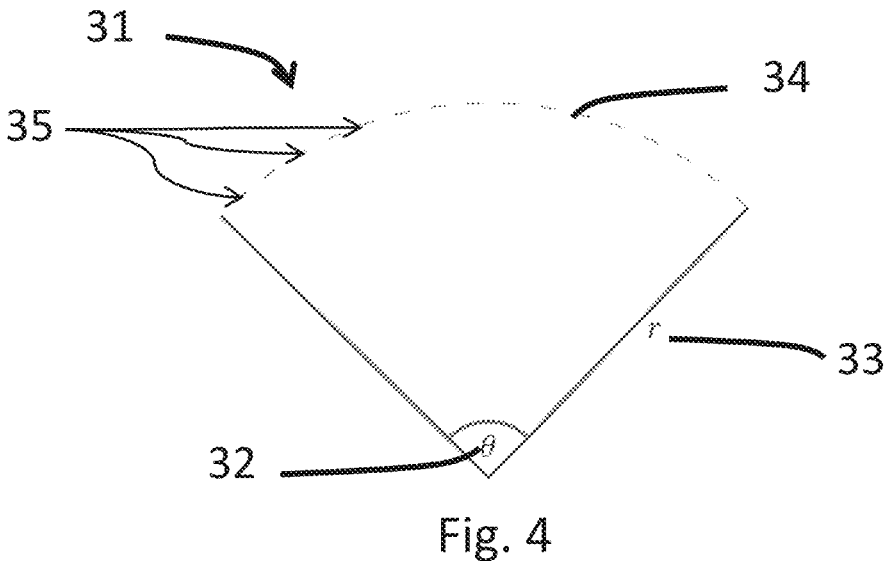
Fig. 4
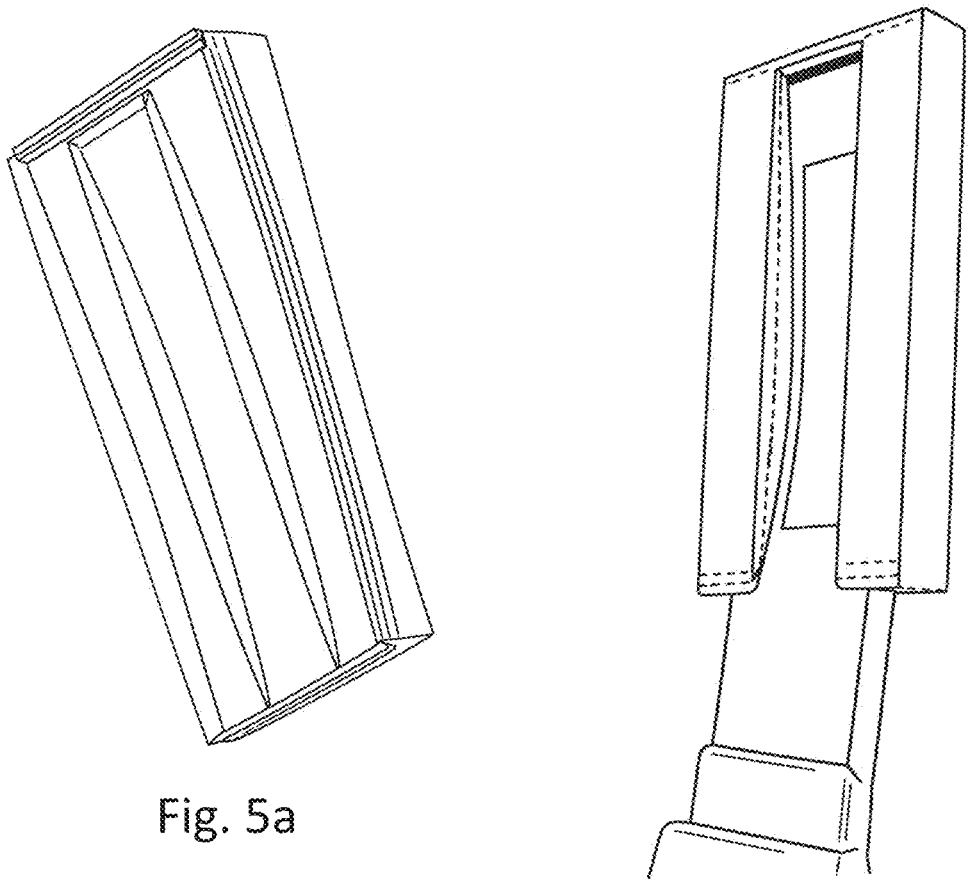
Fig. 5a
Fig. 5b

Beam Angle from Centre [deg]

Inspected θ Shape in Receive [degrees]

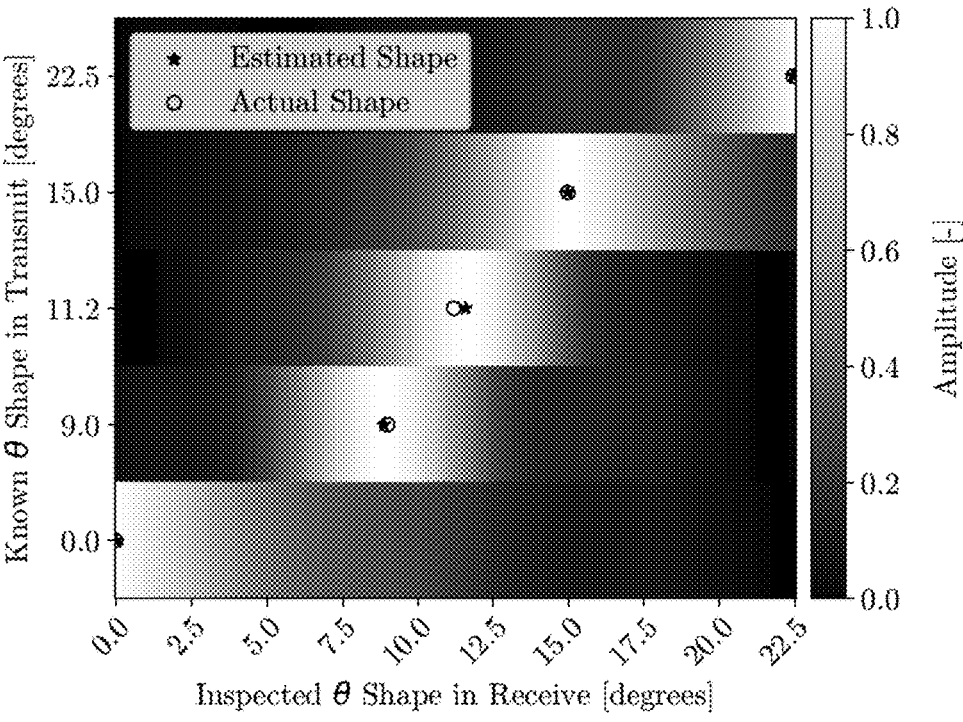
Fig. 11
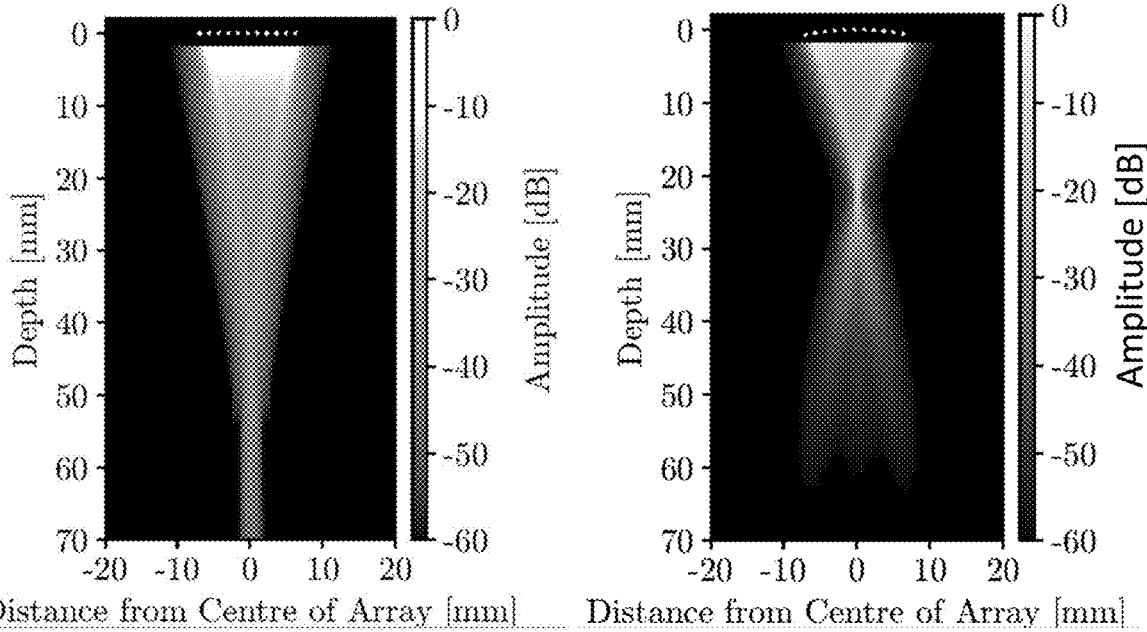
Fig. 12a                    Fig. 12b

FLEXIBLE ULTRASOUND TRANSDUCER

TECHNICAL FIELD OF THE INVENTION

The present invention relates to an ultrasound imaging system comprising a flexible ultrasound device and a shape estimation module adapted to estimate the actual shape of the flexible ultrasound device, and to a method for estimating the actual shape of the flexible ultrasound device.

BACKGROUND OF THE INVENTION

Ultrasound echography is one of the most used diagnostic imaging techniques as it is real-time, safe, low-cost and non-invasive. Conventional ultrasound imaging is usually performed by scanning a medium using sequentially focused beams, each firing allowing the reconstruction of one line of the final image. Data received by a receiver is commonly called pre-beamformed data, and the reconstructed image based on received data is commonly called a beamformed signal or image.

Flexible ultrasound transducer arrays provide a mean to conform the shape of an ultrasound transducer to that of the surface of an object under investigation. Such ultrasound transducers may facilitate the transmission of ultrasound waves from a transmitter, like a probe, to a load because they can be directly coupled to the surface in question. However, effectively focusing the transmitted beam while conforming the ultrasound transducer array shape to the surface of the object requires the position or location of the transducer elements to be accurately known.

Flexible ultrasound transducer arrays facilitate imaging through complex surfaces that were not previously accessible in either the medical or non-destructive testing (NDT) domains using standard array transducers. In the medical domain, imaging through curved surfaces such as the chest or thorax typically requires pressing the rigid transducer against the tissue to force the tissue to conform to the flat shape of the transducer. As such, smaller apertures are typically deployed in medical applications that in turn limits the field of view. In the NDT community, the solution has been to immerse the steel target and array transducer in water and to deploy advanced beamforming strategies to account for refraction at the acoustic interface between the two.

Where the array element positions are consistent during a given acquisition cycle, additional hardware can be coupled to the ultrasound array to determine the relative element positions. Existing solutions, not necessarily in the medical field, provide (or even require) certainty in the element positions and facilitate the transmission of ultrasound in the target but do not provide a robust solution where variation in the element positions of the transducer array may occur. Recent advances in microelectronics indicate that such flexible arrays can be implemented as wearable ultrasound sensors for medical applications. In this case, incorporating additional hardware for array shape estimation creates a burden on the patient as the device becomes too bulky to become wearable itself.

It is possible to estimate the array element positions from artefacts relating to a spatial point of reference located inside the image target such as a point scatterer or plane reflector. Shape estimation in NDT applications has also been proposed by iterating the element positions over a range of shapes and using the shape that maximised the pixel intensity as an indication of the correct shape; however, this is susceptible to interference from other image artefacts.

Alternatively, the time of flight of an ultrasound pulse between element indices has been demonstrated as a tool for shape estimation. In that case the spatial reference point corresponds to the array itself. In such state-of-the-art algorithms a single element is used to transmit while the remaining elements receive. The time of flight of the transmitted pulse to each of the receive element indices is used to fit a polynomial corresponding to the array shape. A disadvantage of this approach is that any artefacts located along the path length between the spatial reference points can introduce uncertainty in the estimated array shape.

It is possible to estimate the array element positions from artefacts relating to a spatial point of reference located inside the image target such as a point scatterer or plane reflector. Shape estimation in NDT applications has also been proposed by iterating the element positions over a range of shapes and using the shape that maximized the pixel intensity as an indication of the correct shape; however, this is susceptible to interference from other image artefacts.

NODA, T. et al. "*Self-shape estimation algorithm for flexible ultrasonic transducer array probe by minimizing entropy of reconstructed image*", 6 Oct. 2019 IEEE International Ultrasonics Symposium, pages 131-134, discloses a shape estimation algorithm for a flexible ultrasound device based on the entropy of a reconstructed image using an assumed array shape. A drawback of this is that the variation across the full image or an ROI within the image should be determined, and that the full image scene must be reconstructed for each assumed array shape, comprising the temporal resolution of the algorithm, requiring a significant amount of computing time and resources. Moreover, for echocardiographic applications the actual shape of the flexible ultrasound device, i.e. the array element positions, may vary as the patient breathes requiring a computationally faster shape estimation algorithm.

CRUZA, Jorge F.; MEDINA-VALDES, Luis; FRITSCH, Carlos. Real time autofocusing hardware for ultrasonic imaging with interfaces. In: 2015 IEEE International Ultrasonics Symposium (IUS). IEEE, 2015. p. 1-4 describes an interactive method for determining a shape metric. The method comprises obtaining a time-of-flight from every array element and scan line to two foci, taking into account refraction. HUNTER, Alan J.; DRINKWATER, Bruce W.; WILCOX, Paul D. Autofocusing ultrasonic imagery for non-destructive testing and evaluation of specimens with complicated geometries. Ndt & E International, 2010, 43.2: 78-85 describes autofocusing based on an assessment of the sharpness of an image for determining a shape metric.

Hence, a drawback of the existing solutions in both the medical and non-medical field for the estimation of an effective shape of an ultrasound transducer array require at least one spatial feature of an image to be optimized with respect to the array shape. The variation in these artefacts depends on the dynamic range and number of focal points in the image.

All the aforementioned reasons call for an ultrasound imaging system and method for at least medical purposes allowing an accurate and reliable estimation of a shape of a flexible or deformable ultrasound transducer array device, in particular to estimate the effective position of the transducer elements defining the array, wherein the computational efficiency may be optimized, fast and robust without—or to a minimal extend—loss of image accuracy and resolution.

SUMMARY OF THE INVENTION

The current invention aims to address the aforementioned drawbacks and to provide a method for estimating an actual shape of a flexible ultrasound device, i.e. an actual shape of the transducer elements array disposed on a flexible supporting platform, without a need of an external image related reference point, and which may be implemented in real time with respect to the image reconstruction.

It is an advantage of embodiments of the present invention that an actual shape of a flexible ultrasound device can be estimated independently of any spatial reference points and can be implemented in real time with respect to the image reconstruction.

It is an advantage of embodiment of the present invention that an echo signal phase variation may be calculated across receive channels rather than in image pixels and/or may be determined across the beam formed envelope, resulting in a reduction of the number of required focal points, which is beneficial for the computational load of the algorithm without compromising the metric accuracy.

It is an advantage of embodiments of the present invention that the method is easy-to-implement, accurate and robust. Embodiments of the present invention are not, or to a minimal extent, sensitive to image artefacts located along the path length of the ultrasound beam and is purely software based so can be easily deployed on the flexible ultrasound device itself.

It is an advantage that no additional hardware, like optical fibres, is required to be coupled to the transducer elements to measure their position or location in situ. By exploiting the echo signal phase variation across the respective receive channels, all information relating to a shape of the ultrasound flexible device may be contained within a set of received echo signals. Therefore, the image target does not need to contain specific artefacts nor does the full image need to be generated for each assumed shape of the flexible ultrasound device, i.e. each investigated array shape.

According to a first aspect, the present invention provides a method for estimating an actual shape of a flexible ultrasound device, wherein the flexible ultrasound device comprises a flexible supporting platform and a plurality of transducer elements disposed in an array configuration on the flexible supporting platform, the method comprising:

a) determining a series of shape metrics based on a predetermined series of assumed shapes of the flexible ultrasound device, wherein, for each assumed shape of the predetermined series of assumed shapes of the flexible ultrasound device, a corresponding shape metric is determined by executing the following steps:

a1) transmitting, based on an assumed shape of the predetermined series of assumed shapes of the flexible ultrasound device and on a first predetermined transmit focus position, a transmit beam focused on the first predetermined transmit focus position by driving a first portion of the plurality of transducer elements based on a transmit delay time;

a2) receiving, by a second portion of the plurality of transducer elements, an echo signal in response to the transmit beam, wherein each transducer element of the second portion of the plurality of transducer elements is electronically connected to a respective receive channel; and a3) calculating, in receive mode, an echo signal phase variation across the respective receive channels by converting the received echo signal into a time delayed echo signal per respective receive channel and quantifying, based on said time delayed echo signal, the echo signal phase variation of the received echo signal across the respective receive channels; and a4) determining a shape metric based on the calculated echo signal phase variation across the respective receive channels for the assumed shape of the predetermined series of assumed shapes of the flexible ultrasound device and the predetermined transmit focus position; and b) selecting the optimal (e.g. smallest or largest) shape metric of the determined series of shape metrics, wherein the assumed shape of the predetermined series of assumed shapes of the flexible ultrasound device corresponding to the optimal shape metric provides an estimation of the actual shape of the flexible ultrasound device.

It is an advantage of the actual shape estimation method that an actual shape of a flexible ultrasound device can be estimated independently of any spatial reference points and can be implemented in real time with respect to the image reconstruction. Indeed, each shape metric is determined based on the calculated echo signal phase variation across the respective receive channels for the selected assumed shape of the predetermined series of assumed shapes.

According to a particular embodiment of the present invention, the steps a1), a2) and a3) are repeated for a second predetermined transmit focus position different from the first predetermined transmit focus position, and wherein the determined shape metric in step a4) is based on a weighted sum of the calculated echo signal phase variations across the respective receive channels for the assumed shape of the predetermined series of assumed shapes of the flexible ultrasound device and respectively the first and the second predetermined transmit focus position of the flexible ultrasound device.

According to a particular embodiment of the present invention, the first and the second portion of the plurality of transducer elements are identical.

According to a particular embodiments of the present invention, the step of quantifying the echo signal phase variation comprises a step of computing a statistical parameter, wherein the statistical parameter is selected from the group consisting of the variance, the covariance, the correlation, the mean, the standard deviation, or the skewness.

According to a particular embodiment of the present invention, the actual shape estimation method further comprises a step of quantizing the time delayed echo signal per respective receive channel before quantifying the echo signal phase variation.

According to a particular embodiment of the present invention, the quantizing step comprising the application of a binary phase descriptor on the time delayed echo signal phase $s_i$ per respective receive channel i at the $k^{th}$ depth, wherein the quantized echo signal phase $b_i$ is defined according to $$b_i = \begin{cases} +1 & \text{if } s_i(k) \geq 0, \\ -1 & \text{if } s_i(k) < 0 \end{cases} \text{ and } \sum b_i^2 = N,$$

wherein N equals the number transducer elements of the second portion, wherein $1 \leq i \leq N$, and wherein k is between 1 and a predetermined number of depth points.

According to a particular embodiment of the present invention, the plurality of transducer elements are arranged in n rows and m columns, wherein $n+m \geq 3$.

According to a particular embodiment of the present invention, the step of selecting the optimal shape metric, corresponding with the smallest or largest shape metric, of the determined series of shape metrics further comprises a step of using a stochastic gradient descent.

The shape metric that is considered the optimal shape metric, corresponding with the smallest or largest shape metric, may depend on the way in which the shape metric is based on, e.g., determined from, the calculated echo signal phase variation across the respective receive channels. As an example, the optimal shape metric may be the smallest shape metric, for example, when said calculated echo signal phase variation is a variance, when the determined shape metric in step a4) is: proportional to the calculated echo signal phase variation; or proportional to the weighted sum of the calculated echo signal phase variations across the respective receive channels mentioned above. In an alternative example, the optimal shape metric may be the largest shape metric, for example, when said calculated echo signal phase variation is a variance, when the determined shape metric in step a4) is: proportional to a reciprocal of the calculated echo signal phase variation; or proportional to the weighted sum of a reciprocal of the calculated echo signal phase variations across the respective receive channels mentioned above. The invention is, however, not limited to a maximum or minimum shape metric, and the shape metric that is selected to be the optimal shape metric may depend on how the shape metric is based on the calculated echo signal phase variation across the respective receive channels.

According to a second aspect of the invention, there is provided an ultrasound imaging system, comprising:
  a flexible ultrasound device, wherein the flexible ultrasound device comprises a flexible supporting platform and a plurality of transducer elements disposed in an array configuration on the flexible supporting platform;
  a data storage unit storing a shape estimation module and configured to store data from the shape estimation module; and
  a data processing unit connected to the flexible ultrasound device and the data storage unit, and adapted to receive data from the flexible ultrasound device and to process the received data;
wherein, when executed, the shape estimation module performs the steps of:
  a) determining a series of shape metrics based on a predetermined series of assumed shapes of the flexible ultrasound device, wherein, for each assumed shape of the predetermined series of assumed shapes of the flexible ultrasound device, a corresponding shape metric is determined by executing the following steps:
    a1) transmitting, based on an assumed shape of the predetermined series of assumed shapes of the flexible ultrasound device and on a first predetermined transmit focus position, a transmit beam focused on the first predetermined transmit focus position by driving a first portion of the plurality of transducer elements based on a transmit delay time;
    a2) receiving, by a second portion of the plurality of transducer elements, an echo signal in response to the transmit beam, wherein each transducer element of the second portion of the plurality of transducer elements is electronically connected to a respective receive channel;
    a3) calculating, in receive mode, an echo signal phase variation across the respective receive channels by converting the received echo signal into a time delayed echo signal per respective receive channel and quantifying, based on said time delayed echo signal, the echo signal phase variation of the received echo signal across the respective receive channels; and
    a4) determining a shape metric based on the calculated echo signal phase variation across the respective receive channels for the assumed shape of the predetermined series of assumed shapes of the flexible ultrasound device and the predetermined transmit focus position; and
  b) selecting the optimal shape metric, corresponding with the smallest or largest shape metric, of the determined series of shape metrics, wherein the assumed shape of the predetermined series of assumed shapes of the flexible ultrasound device corresponding to the optimal shape metric provides an estimation of the actual shape of the flexible ultrasound device.

In a specific embodiment of the present invention, the shape estimation module is adapted to repeat steps a1), a2) and a3) for a second predetermined transmit focus position different from the first predetermined transmit focus position, and wherein the determined shape metric in step a4) is based on a weighted sum of the calculated echo signal phase variations across the respective receive channels for the assumed shape of the predetermined series of assumed shapes of the flexible ultrasound device and respectively the first and the second predetermined transmit focus position of the flexible ultrasound device.

According to a third aspect of the invention, there is provided a computer program comprising instructions to cause the system according to any of aforementioned embodiments to execute the steps of the method according to any of aforementioned embodiments.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 4 is a schematic illustration of the parameters used to characterize a flexible array shape and transducer element position or coordinates;

FIG. 5a illustrates a sleeve to conform a flexible ultrasound transducer array to desired shapes;

FIG. 5b depicts an array being conformed using one of the sleeves as presented in FIG. 5a;

FIG. 11 depicts the values of the shape metric $S_j$ for all ten array shapes recorded before being interpolated with a cubic spline, scaled between zero and one and being inverted, as in FIG. 10, but wherein the experimental data are also with the depth axis limited to $$\pm \frac{\lambda}{2}$$

on either side of the transmit focal depth;

FIG. 12a shows a beam shift phenomenon using pressure fields simulated with Field II software and a flat ultrasound transducer array;

FIG. 12b shows a beam shift phenomenon using pressure fields simulated with Field II software and a curved ultrasound transducer array wherein the opening angle equals $$\frac{\pi}{8};$$

Figure 13:
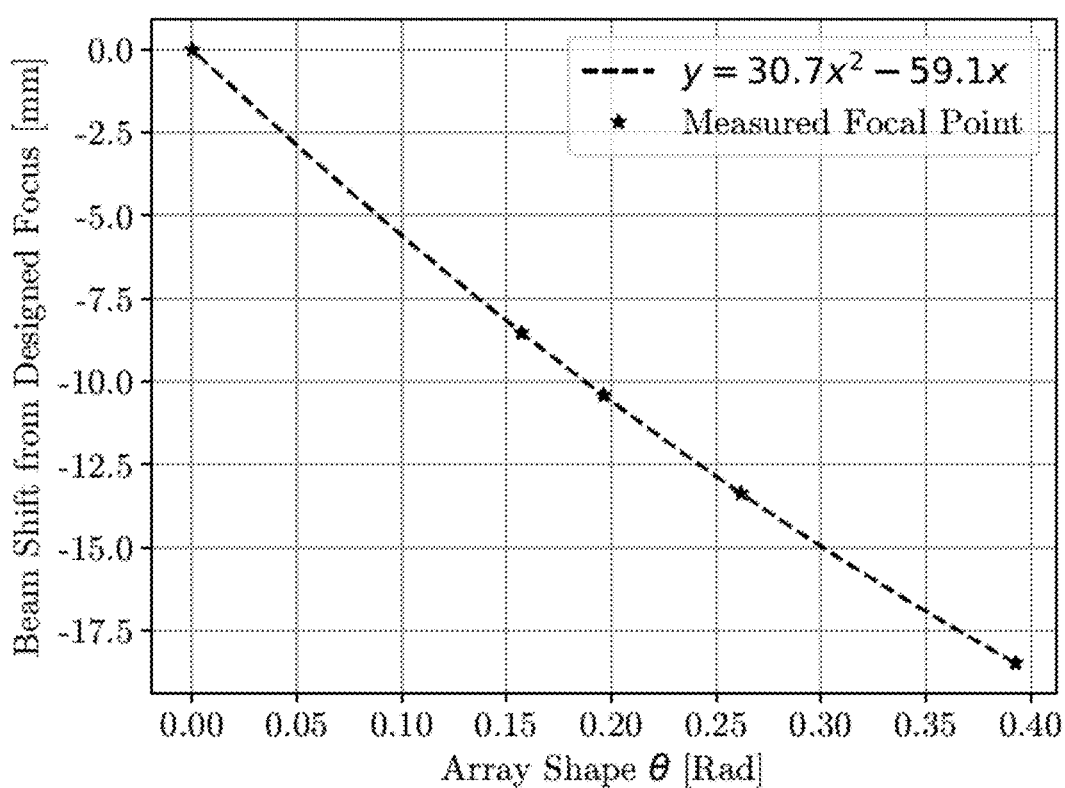
Figure 14:
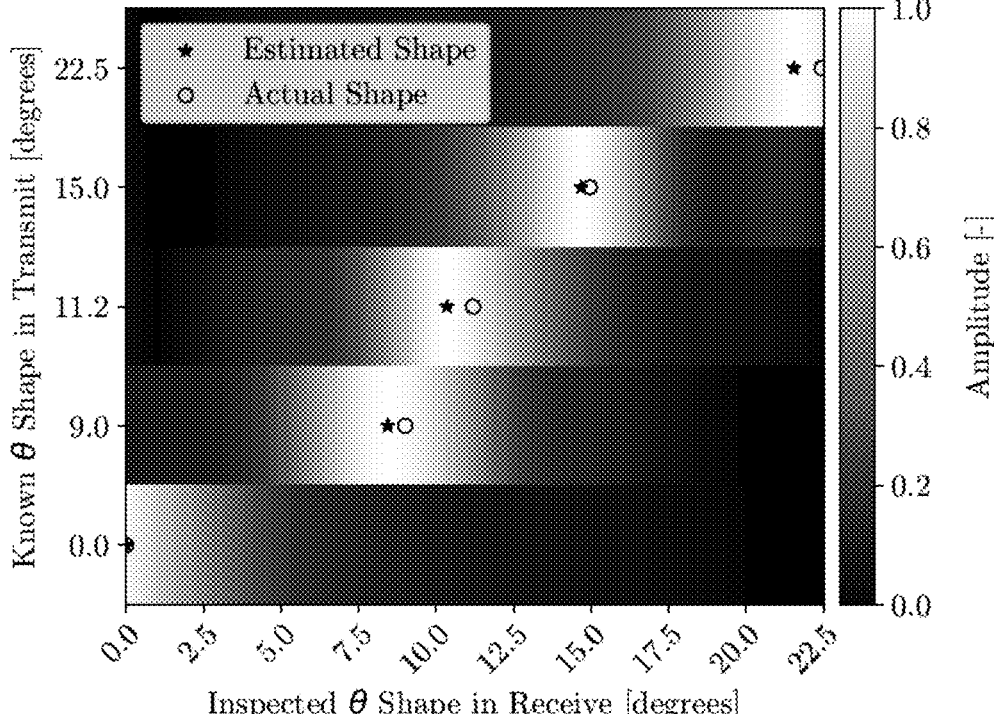
Figure 15:
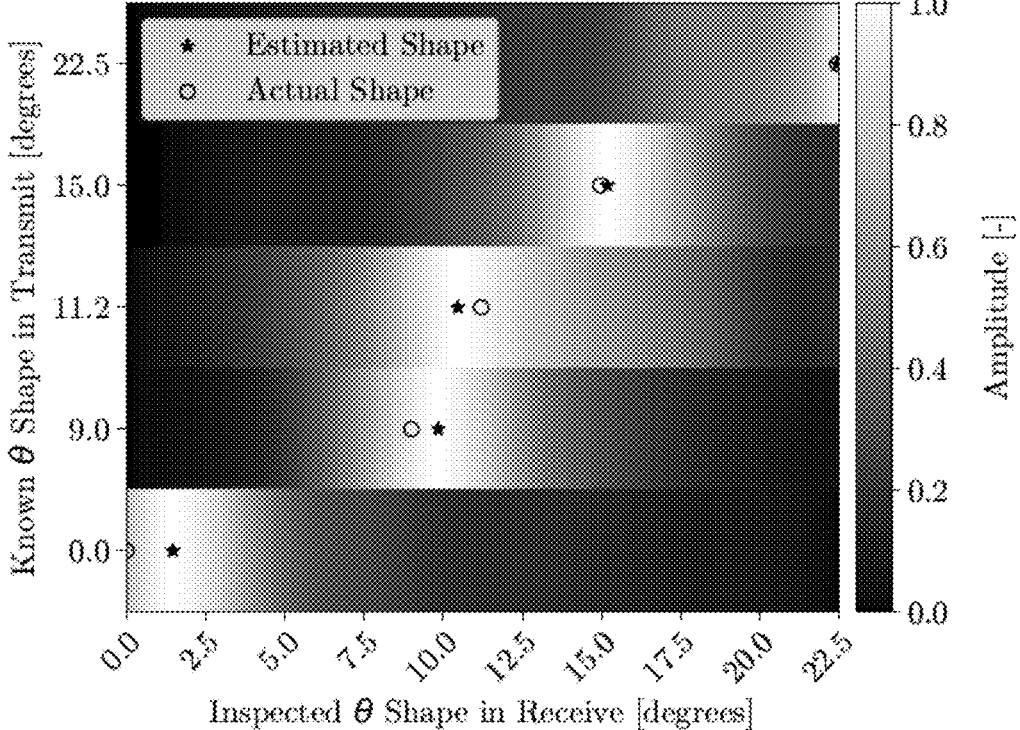

FIG. 13 shows a Beam shift calibration curve determined from simulated pressure fields according to embodiments of the present invention;

FIG. 14 illustrates, for different array shapes, a comparison between the actual shape of an ultrasound transducer array and a determined shape according to embodiments of the present invention; and FIG. 15 illustrates, for different array shapes, a comparison between the actual shape of an ultrasound transducer array and a determined shape according to embodiments of the present invention;

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B. Furthermore, the terms first, second, third and the like in the description and in the claims, are used for distinguishing between similar elements. It is to be understood that the terms so used may be interchangeable under appropriate circumstances. In the drawings, like reference numerals indicate like features; and, a reference numeral appearing in more than one figure refers to the same element. Furthermore, while some embodiments described herein include some but not other features included in other embodiments, combinations of features of different embodiments are meant to be within the scope of the invention, and form different embodiments, as would be understood by those in the art.

Unless indicated otherwise, when in the present application reference is made to "a flexible ultrasound device", reference may be made to a transducer comprising a flexible supporting platform and a plurality of transducer elements disposed in an array configuration on the flexible supporting platform. Hence, when reference is made to "a flexible ultrasound device", reference may be made to a flexible ultrasound transducer array.

Unless indicated otherwise, when reference is made to "a shape of an ultrasound transducer array", reference may be made to a shape of the flexible supporting platform on which transducer elements are disposed in an array configuration. Hence, when reference is made to "a shape of an ultrasound transducer array", reference may be made to the shape of the array expressed by shape-related parameters like the opening angle of the flexible array and the radius from which the spatial position or location, expressed in coordinates, of the transducer elements defining the array may be determined, wherein the position or location is expressed relative to a reference point of the array, like, without being limited thereto, the array apex. According to embodiments of the present invention, the coordinates defining the position or location of the transducer elements, may also be obtained directly, i.e. without prior knowledge of the opening angle and/or radius of the array.

Unless indicated otherwise, when reference is made to "an actual shape" of a flexible ultrasound device, reference may be made to the current or present shape of the flexible ultrasound device which may be estimated according to embodiments of the present invention.

Unless indicated otherwise, when reference is made to "echo signal phase variation" across receive channels, reference may be made to echo signal phase coherence across receive channels.

Estimating an actual shape of a flexible transducer element, i.e. estimating the position or coordinates of the transducer elements, is of utmost importance for ultrasound image construction when dealing with ultrasound devices, in particular phased-array ultrasound transducers.

Indeed, the energy transmitted from a first portion of transducer elements of the flexible ultrasound device, having the plurality of transducer elements configured in an array configuration, is focused by applying a predetermined transmit delay time to each first portion transducer element with respect to a transducer specified reference point, like for example, without being limited thereto, the array apex. These predetermined transmit delay times may be calculated based on the predetermined or derived transducer element coordinates and the speed of sound in the load medium. When these delays are applied across the aperture, the transmitted signals, defining the transmit beam, arriving at the desired focus are in phase resulting in constructive interference, maximising the energy intensity at the focus or focal point. Contrary, if uncertainty is introduced to the transducer element coordinates applying a time delay based on the expected transducer element coordinates, then the transmitted signals arrive out of phase from one another. This spreads the total energy of the transmit beam across a larger volume as fewer signals constructively interfere at the desired position. This uncertainty translates to a defocussing or blurring of the images reconstructed from the received echo signal across the receive channel data.

The fundamental idea behind embodiments of the current invention is related to the variation in the echo signal phase across the receive aperture, defined by a second portion of transducer elements of the flexible ultrasound device, and their respective receive channels. This echo signal phase variation may be optimized, e.g. minimized or maximized, at the focus or focal point (also referred to as transmit focus position) of the transmitted beam. If uncertainty is introduced into the transducer elements coordinates or position, then the variation in the echo signal phase across the respective receive channels may change, e.g. increase or decrease. In light of this, embodiments of the present invention aim to measure this echo signal phase variation within a set beam space for an assumed array shape to determine a shape metric of the flexible ultrasound transducer array, for example, a relative value describing the assumed shape of the ultrasound flexible transducer array.

Figure 1A:
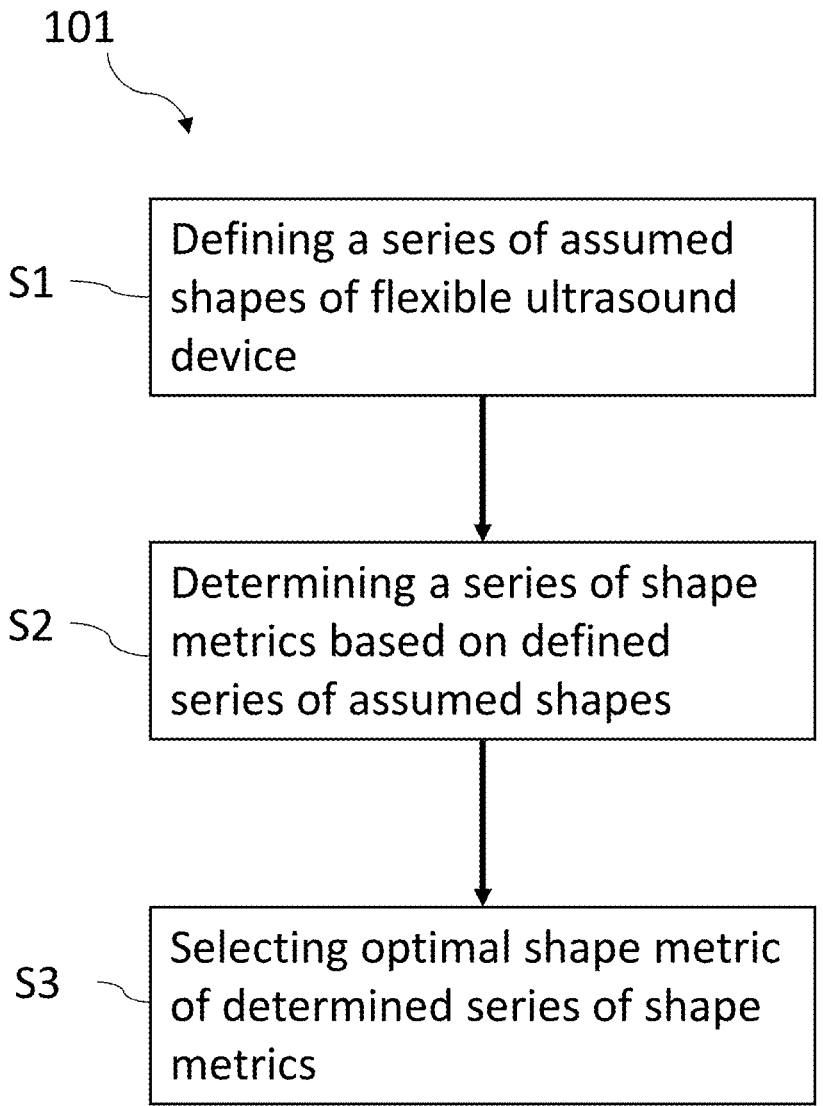
FIG. 1a depicts a flowchart of an actual shape estimation algorithm according to embodiments of the present invention.

Referring to FIG. 1a a flowchart 101 of an actual shape estimation method according to embodiments of the present invention is shown. In a first step S1, a series of assumed shapes of the flexible ultrasound device is predetermined or defined. In a second step S2, a series of shape metrics will be determined based on the predetermined series of assumed shapes of the flexible ultrasound device. In a third step S3, the optimal shape metric, corresponding with the smallest or largest shape metric—depending on how the shape metric is defined, of the in step S2 determined series of shape metrics will be selected. This selected optimal shape metric corresponds with an assumed shape of the predetermined series of assumed shapes of the flexible ultrasound device and provides an estimation of the actual shape of the flexible ultrasound device.

Figure 1B:
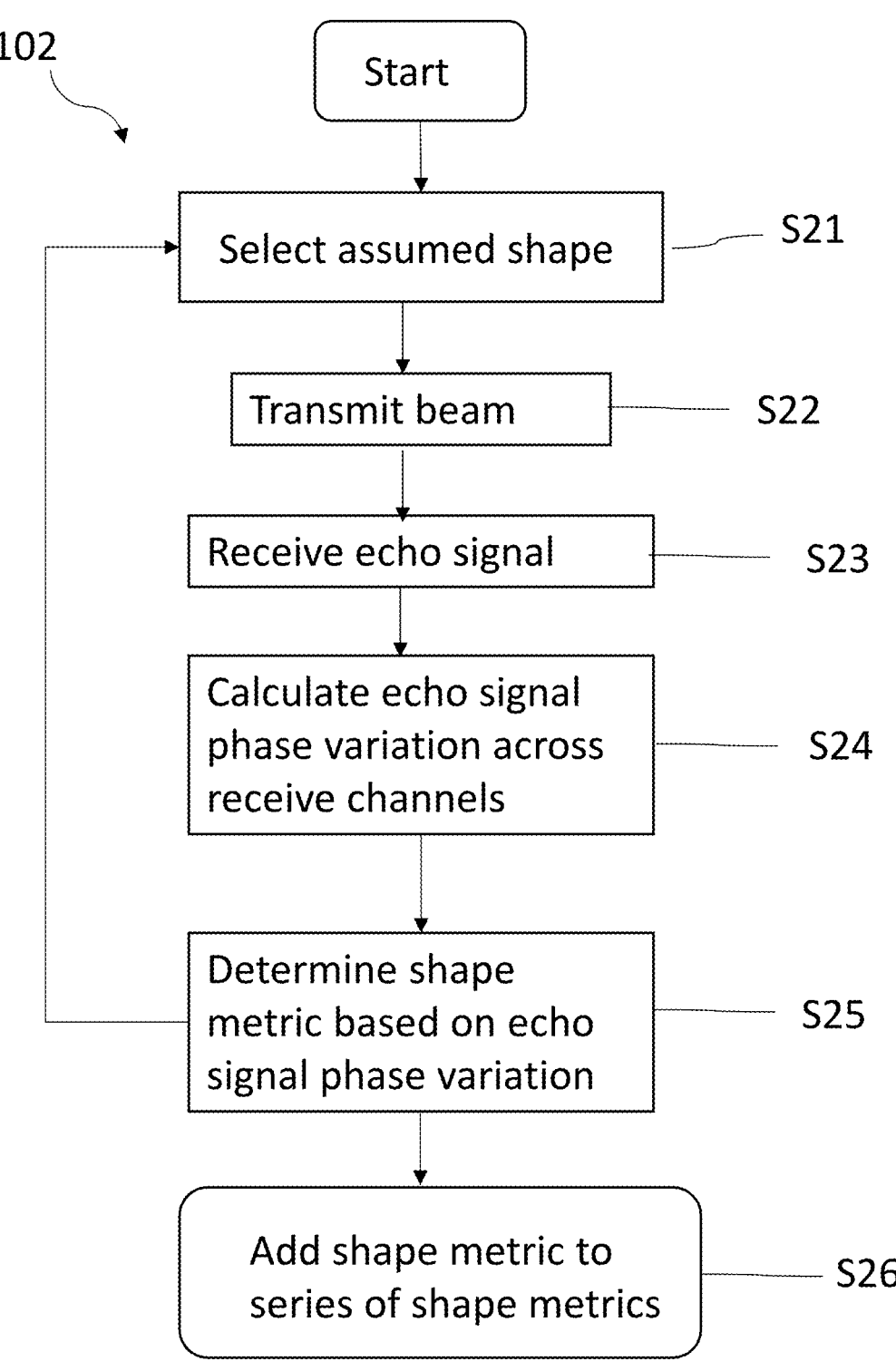
FIG. 1b shows a flowchart on the steps performed to determine a series of shape metrics according to embodiments of the present invention.

Referring to FIG. 1b a flowchart 102 on the steps performed to determine a series of shape metrics S2 according to embodiments of the present invention is illustrated. In step S21 an assumed shape of the predetermined series of assumed shapes of the flexible ultrasound device is selected. Based on this selected assumed shape and a predetermined transmit focus position, a transmit delay time for driving a first portion of the transducer elements is determined and applied for transmitting a transmit beam S22. Next, an echo signal in response to the transmit beam is received S23 by a second portion of the transducer elements, wherein each transducer element of the second portion of transducer elements is electronically connected to a respective receive channel. Next, in receive mode, an echo signal phase variation across the respective receive channels is calculated S24. This calculation step S24 comprises a converting step to convert the received echo signal into a time delayed echo signal per respective receive channel, and a quantifying step wherein the echo signal phase variation across the respective receive channels is quantified based on the time delayed echo signal. Finally, a shape metric based on the calculated S24 echo signal phase variation across the respective receive channels for the assumed shape of the flexible ultrasound device and the predetermined transmit focus position is determined S25. The determined shape metric is added to a series of determined shape metrics S26. Thereafter, the steps S21, S22, S23, S24 and S25 may be repeated for another assumed shape of the predetermined series of assumed shapes of the flexible ultrasound device.

Figure 1C:
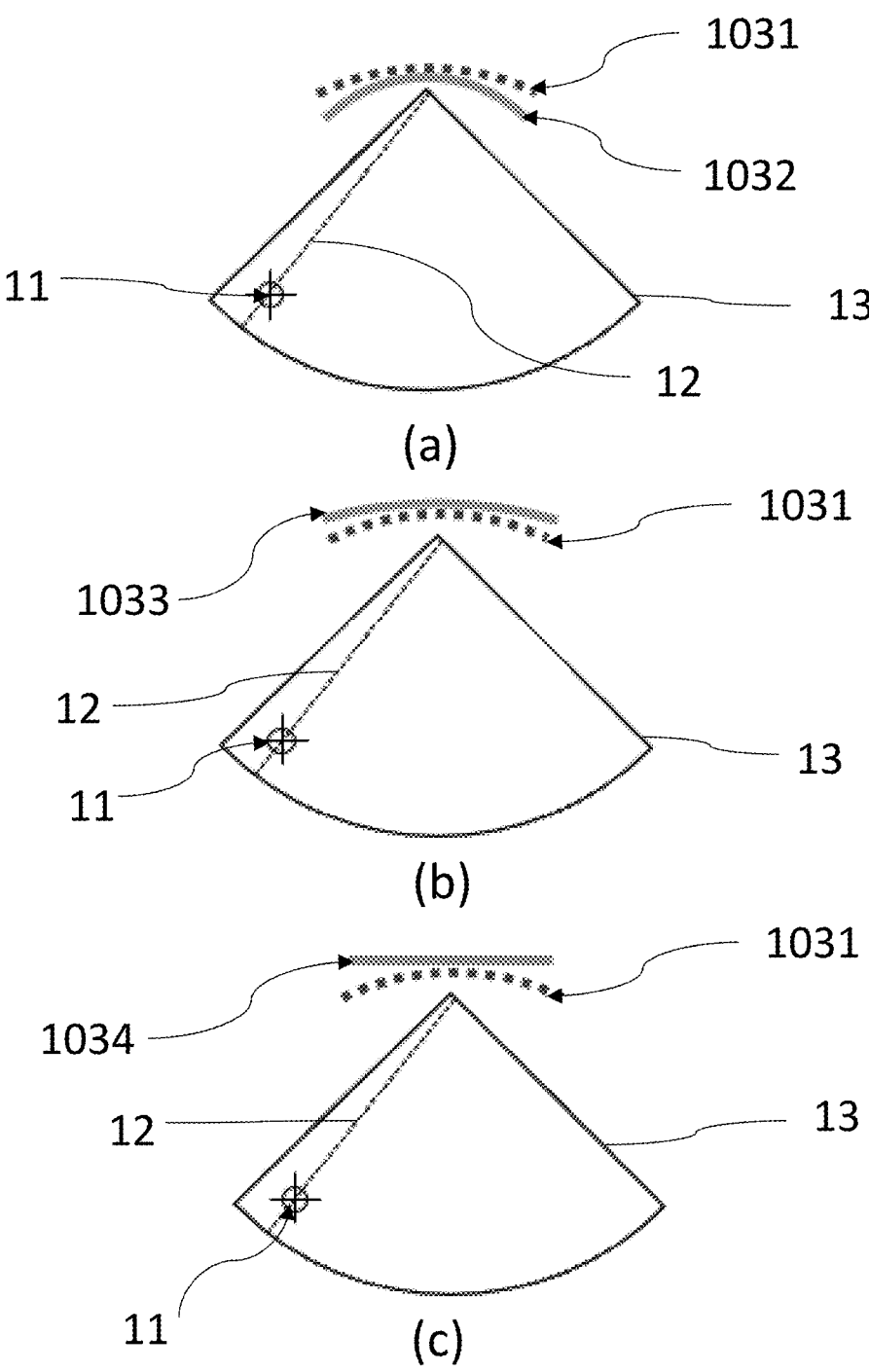
FIG. 1c is a schematic illustration of three beam spaces comprising a transmit beam and a transmit focus position to illustrate at least part of the shape estimation method according to embodiments of the present invention.

Referring to FIG. 1c (a), (b) and (c), schematic illustrations of an ultrasound image comprising a transmit beam 12 defining a beam space 13 and having a transmit focus position 11, are shown for three assumed shapes 1032, 1033, 1034 of a flexible ultrasound device. The to be estimated actual shape 1031 of the flexible ultrasound device is also shown in each illustration (a), (b) and (c). For clarity purposes, the assumed shapes and actual shape of the flexible ultrasound device are illustrated in 2D. An actual shape estimation method of a flexible ultrasound device according to embodiments of the present invention may be further explained by referring to FIG. 1c. A predetermined series of assumed shapes of the flexible ultrasound device may comprise the assumed shapes 1032, 1033, 1034. For each of these assumed shapes a shape metric is determined by executing the following steps on an ultrasound imaging system according to embodiments of the present invention:

selecting an assumed shape, for example the assumed shape 1032 as illustrated in FIG. 1c (a);

transmitting S22, based on the assumed shape 1031 of the predetermined series of assumed shapes of the flexible ultrasound device and on a first predetermined transmit focus position 11, a transmit beam 12 focused on the predetermined transmit focus position 11 by driving a first portion of the transducer elements of the flexible ultrasound device based on a transmit delay time;

receiving S23, by a second portion of the transducer elements, an echo signal in response to the transmit beam 12, wherein each transducer element of the second portion is electronically connected to a respective receive channel;

calculating S24, in receive mode, an echo signal phase variation across the respective receive channels by converting the received echo signal into a time delayed echo signal per respective receive channel and quantifying, based on said time delayed echo signal, the echo signal phase variation of the received echo signal across the respective receive channels; and determining S25 a shape metric based on the calculated echo signal phase variation across the respective receive channels for the assumed shape 1032 of the predetermined series of assumed shapes of the flexible ultrasound device and the predetermined transmit focus position 11.

Hence, once a shape metric is determined for the assumed shape 1032 of the flexible ultrasound transducer as illustrated in FIG. 1c (a), the aforementioned steps may be repeated for the assumed shape 1033 as illustrated in FIG. 1c (b) and for the assumed shape 1034 as illustrated in FIG. 1c (c). This results in a determined series of shape metrics. By selecting the optimal metric, corresponding with the smallest or largest shape metric—depending on how the shape metric is defined, of the determined series of shape metrics, an estimation of the actual shape 1031 of the flexible ultrasound device may be obtained since the assumed shape of the predetermined series of assumed shapes of the flexible ultrasound device corresponding to the optimal shape metric provides an estimation of the actual shape of the flexible ultrasound device.

Figure 1D:
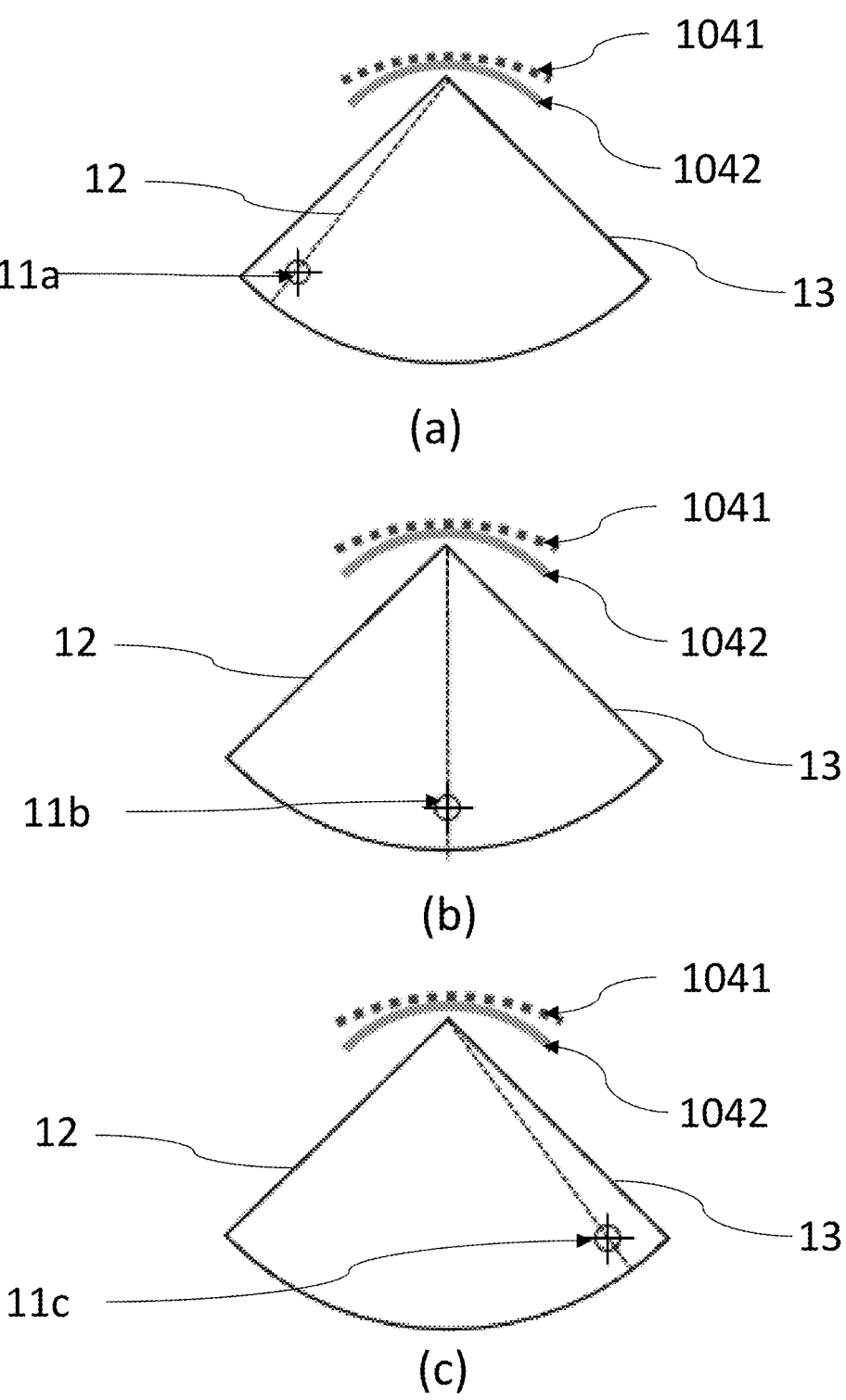
FIG. 1d is a schematic illustration of three beam spaces comprising a transmit beam and a transmit focus position to illustrate at least part of the shape estimation method according to embodiments of the present invention.

According to embodiments of the present invention and as illustrated in FIG. 1*d*, the steps of transmitting a transmit beam S22, receiving an echo signal S23 and calculating, in receive mode, an echo signal phase variation across receive channels S24 for an assumed shape of the flexible ultrasound device, may be repeated for at least a second predetermined transmit focus position for the same assumed shape before selecting another assumed shape predetermined series of assumed shapes of the flexible ultrasound device. As illustrated in FIG. 1*d* (a), (b) and (c), the same assumed shaped 1042 is used when performing the aforementioned steps S22, S23 and S24; however, after executing these steps for a first predetermined transmit focus position 11*a* in the image line 12, a second predetermined transmit focus position 11*b* in the image line 12 is selected and the steps S22, S23 and S24 are performed to determine an echo signal phase variation across receive channels. In this example, a third predetermined transmit focus position 11*c* is selected for the assumed shape of the flexible ultrasound device and the steps S22, S23 and S24 are repeated to calculate an echo signal phase variation across the respective receive channels. The shape metric is determined S25 based on a weighted sum of the calculated echo signal phase variations across the respective receive channels for the assumed shape and the respective first 11*a*, second 11*b* and third 11*c* transmit focus positions. Thereafter, a second assumed shape of the flexible ultrasound device may be selected from the predetermined series of assumed shapes of the flexible ultrasound device to execute the aforementioned steps in order to determine another shape metric.

According to embodiments of the present invention, a transmitted beam may be focused on a predetermined transmit focus position by driving a first portion of the transducer elements of the flexible ultrasound device based on a transmit delay time. This transmit delay time may be predetermined or defined based on an assumed shape of the flexible ultrasound device and the predetermined transmit focus position. An echo signal in response to the transmit beam is received by a second portion of the plurality of transducer elements of the flexible ultrasound device. According to embodiments of the present invention, the first portion of the plurality of transducer elements may be identical or different to the second portion of plurality of transducer elements.

Figure 2A:
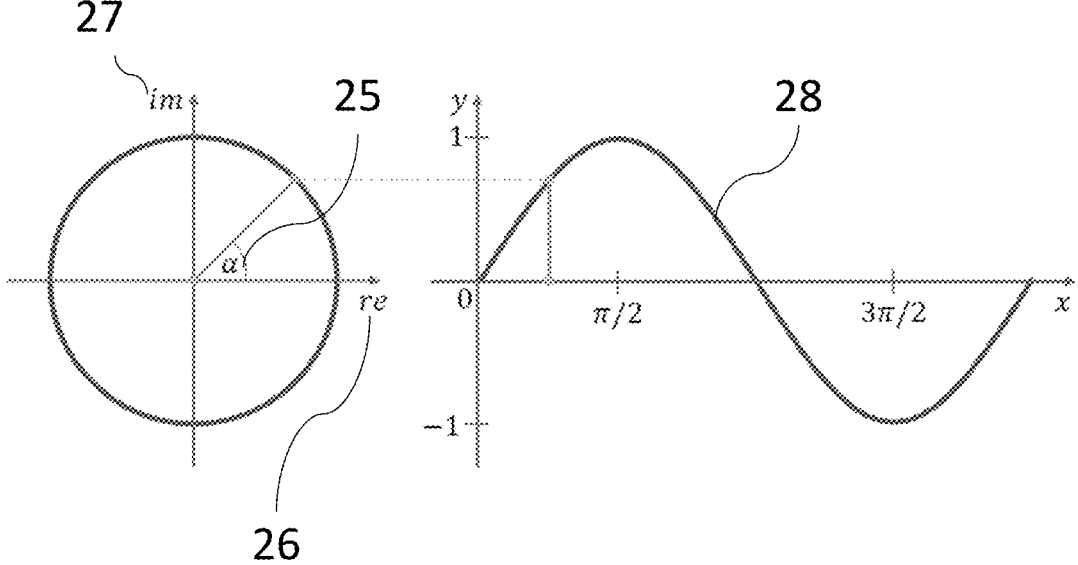
FIG. 2a illustrates a phase diagram of a sine wave.

The signal phase of a received echo signal, also referred to as echo signal phase, may be characterised as the angle α between the real (re) axis 26 and the imaginary (im) axis 27 of the echo signal 28, as illustrated in FIG. 2*a*. The value of this angle α 25 may be determined from the inverse tangent of the ratio between the in-phase and quadrature components of the analytic signal expression.

Figure 2B:
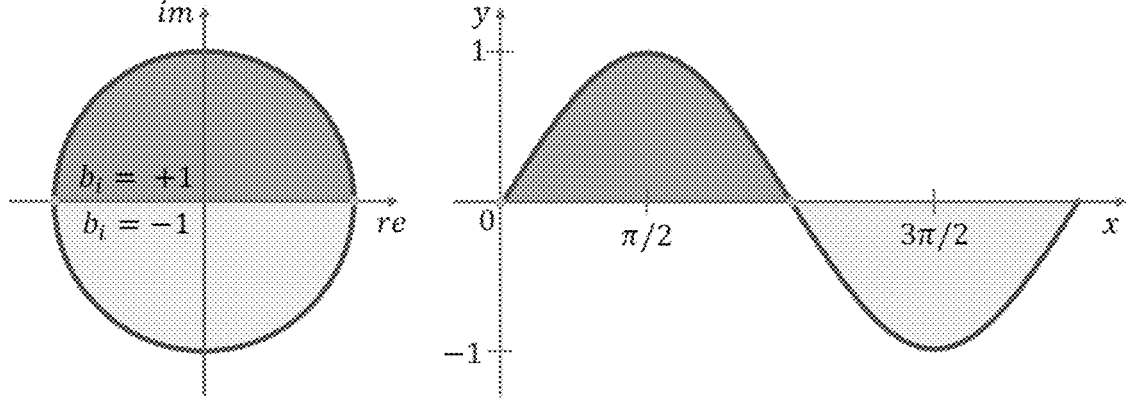
FIG. 2b illustrates a phase diagram of a sine wave of FIG. 2a in corresponding sign bit values.

According to embodiments of the present invention, the echo signal phase α 25 may be quantized to define it with respect to the signal polarity, as illustrated in FIG. 2*b*, wherein the echo signal phase α may be assigned to one bit value of a two sign bit, i.e. +1 or −1 (see Equation 1), depending on the value of the time delayed echo signal phase $s_i$ per respective receive channel i at the $k^{th}$ depth. In particular, the quantized echo signal phase $b_i$ of a received echo signal may be expressed as $$b_i = \begin{cases} +1 & \text{if } s_i(k) \geq 0, \\ -1 & \text{if } s_i(k) < 0 \end{cases} \tag{1}$$

where $s_i(k)$ is the value of the receive channel data at the $i^{th}$ receive channel and the $k^{th}$ depth. In this way, a sign coherence factor may be defined wherein the sign coherence factor may be a measure of the spread of phase sign bits across N receive channels. N may be at least equal or larger than one, preferably larger than two, and wherein 1≤i≤N, and wherein k is between 1 and a predetermined number of depth points. The number and location (or position) of the depth points within the beam space may be user-defined, and may be defined depending on the applicable wavelength and their configuration (or spacing) along the depth dimension. For example, in the time domain, at least fifteen (15) samples or depths per wavelength may be needed to capture a variation in a single wavelength. This wavelength is determined from the frequency of the transmitted signal and the speed of sound in the medium.

The computational advantage of applying a two sign bit quantization step or a binary phase description across N receive channels is that $\Sigma b_i^2 = N$, meaning that the individual bits do not need to be stored in a memory linked to a processing unit of the system. The variation of the signal phase of the received echo signal across the receive channels may therefore be expressed as a statistical parameter, for example the variance, the mean, the correlation, the standard deviation or the skewness, without being limited thereto. Hence, when applying the aforementioned binary phase description to quantize the phase of the received echo signal across the receive channels, the variance $\sigma^2$ may therefore become a function of the mean of the sign bits (see Equation 2), i.e.

$$\sigma^2 = 1 - \left(\frac{1}{N}\sum_{i=1}^{N} b_i\right)^2 \tag{2}$$

In order to characterize an echo signal phase variation across the respective receive channels for a series of transmit beams based on one assumed shape j of the flexible ultrasound device but having each a different focal point or transmit focus position, the echo signal phase variation related to said assumed shape j in the beam space may be defined by a shape metric $S_j$, also referred to as an array shape metric, wherein the shape metric $S_j$ is based on a weighted sum of the calculated echo signal phase variations across the receive channels for the selected assumed shape and the respective transmit focal position of the flexible ultrasound device.

Figure 3:
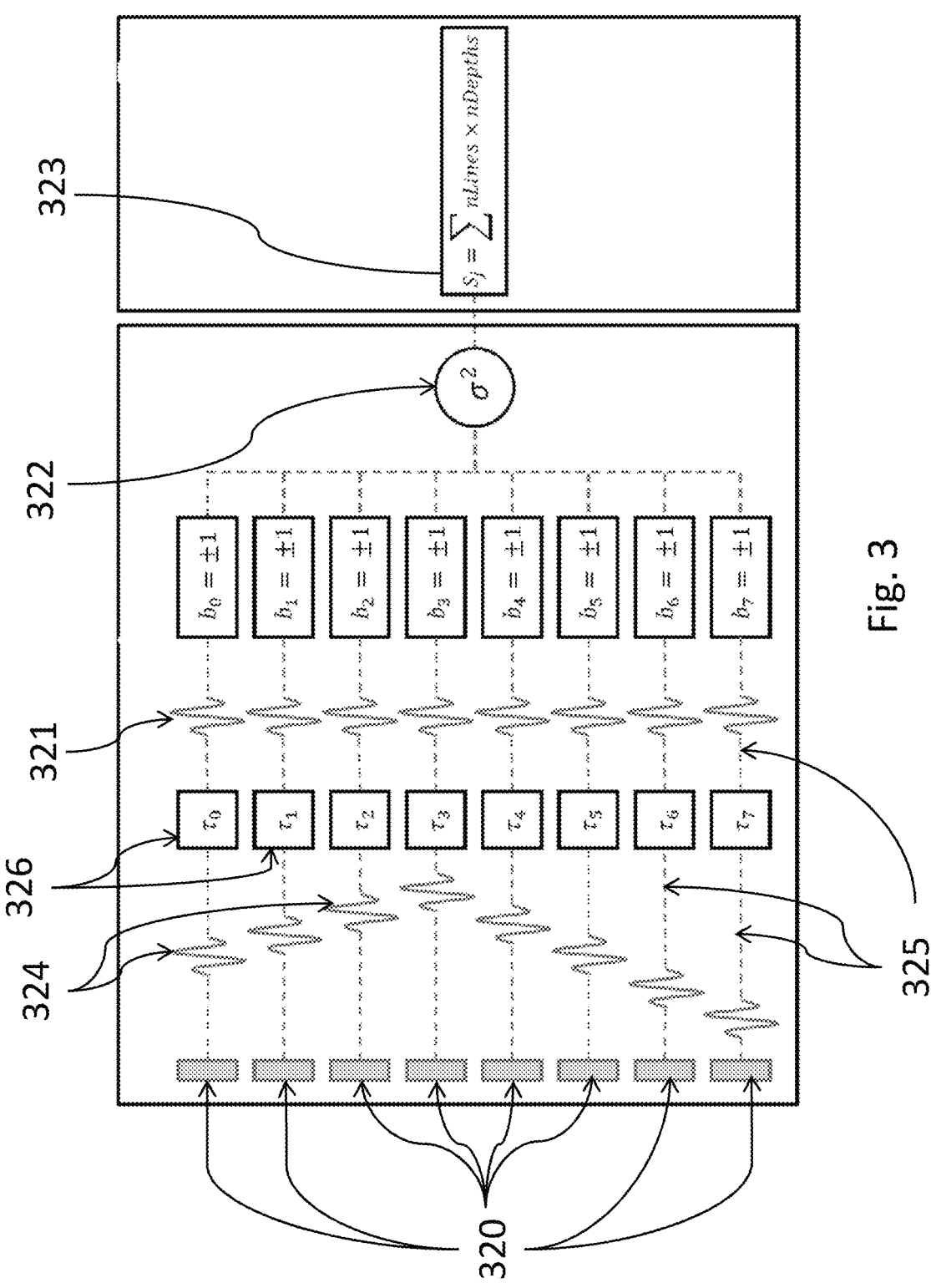
FIG. 3 is a schematic illustration outlining the computation of a shape metric $S_j$ of the $j^{th}$ shape of the ultrasonic transducer defined according to embodiments of the present invention.

Reference is made to FIG. 3 to schematically illustrate at least a portion of the steps to determine a shape metric $S_j$ according to embodiments of the present invention. In this example, the second portion 320 of the plurality of transducer elements comprises eight (8) transducer elements each being electronically connected to a respective receive channel 325. The transducer elements of the second portion 320 of the plurality of transducer elements and their respective receive channels 325 are configured to receive and communicate a received echo signal 324 to a data processing unit (not shown in FIG. 3) of an ultrasound imaging system according to embodiments of the inventions. The data processing unit is connected to the flexible ultrasound device and a data storage unit, and adapted to receive data from the flexible ultrasound device and processing the received data. The flexible ultrasound device, the data storage unit and the data processing unit define an ultrasound imaging system according to embodiments of the present invention. When a shape estimation module, stored in the data storage means, is executed, the following steps are performed:

determining a series of shape metrics $S_j$ based on a predetermined series of assumed shapes (having an assumed shape ID j, wherein $1 \le j$) of the flexible ultrasound device, wherein, for each assumed shape j of the predetermined series of assumed shapes of the flexible ultrasound device, a corresponding shape metric $S_j$ is determined by executing the following steps:

transmitting, based on an assumed shape j of the predetermined series of assumed shapes of the flexible ultrasound device and on a first predetermined transmit focus position, a transmit beam focused on the predetermined transmit focus position by driving a first portion of the transducer elements of the flexible ultrasound device based on a predetermined transmit delay time;

receiving, by a second portion 320 of the plurality of transducer elements, an echo signal 324 in response to the transmit beam, wherein each transducer element of the second portion 320 of the plurality of transducer elements is electronically connected to a respective receive channel 325;

calculating, in receive mode, an echo signal phase variation across the respective receive channels 325 by converting the received echo signal 324 into a time delayed echo signal 321 per respective receive channel 325 and quantifying, based on said time delayed echo signal 321, the echo signal phase variation 326 of the received echo signal 324 across the respective receive channels; and determining 323 a shape metric $S_j$ based on the calculated echo signal phase variation 322 across the respective receive channels 325 for the assumed shape j of the predetermined series of assumed shapes of the flexible ultrasound device and the predetermined transmit focus position; and selecting, when a series of shape metrics $Sj$ is determined, the optimal shape metric, corresponding with the smallest or largest shape metric—depending on how the shape metric is defined, of the determined series of shape metrics, wherein the assumed shape of the predetermined series of assumed shapes of the flexible ultrasound device corresponding to the optimal shape metric provides an estimation of the actual shape of the flexible ultrasound device.

Referring to FIG. 3, the quantifying step when calculating an echo signal phase variation across the respective receive channels 325, in receive mode, comprises the calculation of a quantized echo signal phase $b_i$ per receive channel, i.e. wherein i is between zero (for the first respective receive channel) and seven (for the eighth respective receive channel).

Further referring to FIG. 3, the conversion of the received echo signal 324 into a time delayed echo signal 321 by applying a receive delay time $\tau_i$ per respective receive channel, wherein i refers to a respective receive channels, is indicated with boxes 326 comprising a receive delay time $\tau_i$ parameter. According to embodiments of the present invention, the transmit delay time applied to the first portion of the plurality of transducer elements may be equal or different to the applied receive delay time applied per receive channel in receive mode. The determined or calculated transmit delay time per transducer element of the first portion of the plurality of transducer elements may be defined by the assumed shape of the predetermined series of assumed shapes of the flexible ultrasound device and the first predetermined transmit focus position. Hence, the transmit delay time may be determined based on corresponding coordinates of the first portion transducer elements and the predestined transmit focus position (or focal point of the transmit beam) relative to the array apex. Instead of the array apex, another reference point related to the array of transducer elements may also be applied. The transmit delay times or delays may be used to identify the time samples in the receive channel data that would align the phase of the samples if the correct transducer element coordinates were provided.

The echo signal phase variation 322, also referred to as echo signal phase coherence, of received echo signal 324 across the receive channels 325 may be statistically expressed by determining the variance at at least one, preferably at each, transmit focus position of the transmit beam.

According to embodiments of the present invention wherein the echo signal phase variation 322 is based on a plurality of transmit focus positions, its calculation may be performed in parallel via a general purpose graphics processing unit, like a GP-GPU, and thereafter accumulated to determine a shape metric $S_j$ for the $j^{th}$ assumed shape of the flexible ultrasound device, in particular a shape of the array configuration of the plurality of transducer elements. The determined shape metric $S_j$ can then be stored in a data storage means or unit of an ultrasound imaging system according to embodiments of the present invention. The data storage unit is electronically connected to a data processing unit adapted to executed a shape estimation module comprising method steps according to embodiments of the present invention.

For example, the data processing unit may be a processor comprised in a computing device and the data storage unit may be a memory comprised in said computing device and which is electronically connected to the data processing unit. A flexible ultrasound device, in particular a flexible supporting platform and a plurality of transducer elements disposed in an array configuration on the flexible supporting platform, may be electronically connected to at least the data processing unit such that data can be transferred from the plurality of transducer elements to the data processing unit. The number of parallel processes may be equal to the product of the number of image lines in the sector (also referred to as beam space) and the number of predetermined depth focal points per image line.

Since the shape metric $S_j$ measures the echo signal phase variation across the respective receive channels rather than the echo signal phase variation in image pixels, the number of focal points can be significantly reduced. This has the technical advantage of reducing the computational load when implementing a method according to embodiments of the invention in comparison with a solution which makes use of artefacts in a region of interest in the reconstructed image from the received echo signals.

In order to demonstrate the technical advantages of the present invention, a flexible ultrasound device (also referred to as flexible ultrasound transducer) comprising a flexible supporting platform and a plurality of one hundred twenty-eight (128) transducer elements configured in a one-dimensional (1D) array configuration on the flexible supporting platform, was used to acquire all the test results presented below. This flexible ultrasound device (Olympus, MA, USA) has an array centre frequency of 2.5 MHz and was acoustically matched to water. The flexible ultrasound device was designed with an element pitch of λ/1.5 (≈0.41 mm) to increase the array footprint while maintaining reasonable steering capability. The array controller used to manipulate the pressure field transmitted from the flexible device was an FIToolbox (Diagnostic Sonar Ltd, Scotland). There were hundred twenty-eight (128) channels electronically connected to the 128 array transducer elements and accessible in both transmission and receive mode, hence the full device or array aperture was addressed during both processes.

This demonstration flexible ultrasound device could not undergo large values of strain, limiting the range of shapes of the device that could be investigated. Given this limitation and with the aim to investigate flexible array imaging for transthoracic echocardiography, only strains resulting in concave shapes were applied. Hence, for the testing of embodiments of the present invention, each predetermined assumed shape of the flexible ultrasound device was modelled using a quadratic function with respect to an opening angle θ (expressed in radians) 32 and a radius r 33 of a circular segment 31 defined by the transducer elements 35, as schematically illustrated in FIG. 4. Assuming that an arc length 34 defined by the 1D array of transducer elements or segment of transducer elements is held constant, i.e. the product of the number of transducer elements in 1D times the aforementioned element pitch, it may be understood that if the opening angle θ 32 defined by the array of transducer elements decreases that the shape of the array of transducer elements, hence flexible ultrasound device, becomes more flat. As such, an opening angle θ 32 of zero (0) radians defines a flat array shape, i.e. an array shape wherein the radius r 33 is infinite.

For the tests as described below, the arc length 34 of the segment of transducer elements was set by the length of the active aperture of the flexible ultrasound device, i.e. 128× 0.41=52.48 mm. Five (5) values of the opening angle θ 32 and radius r 33 were considered and listed in Table I.

TABLE I

| Opening angle θ [radians] | Opening angle θ [degrees] | Radius r [mm] |
|---|---|---|
| 0 | 0 | Infinite |
| π/20 | 9.0 | 334.1 |
| π/16 | 11.3 | 267.3 |
| π/12 | 15.0 | 200.5 |
| π/8 | 22.5 | 133.6 |

To conform the demonstration flexible ultrasound device to desired shapes during experimental acquisition, five (5) sleeves were designed in SolidEdge (Siemens, CA, USA). An illustration of such a sleeve is provided in FIG. 5a. These were exported to .stl format using the minimum tolerance value of 0.001 millimeters (mm) before being 3D printed at KULeuven FabLab facility. The parts were orientated during the printing process such that uncertainty in the curved surface was minimized. A depiction of the array being conformed using one of said sleeves is presented in FIG. 5b. Gel couplant was used to fill the gap between the array surface and the tissue-mimicking phantom where care was taken to prevent air bubbles from entering the gel layer. The tissue-mimicking phantom model 055 (CIRS, VA, USA) was used to acquire data corresponding to a scattering medium.

Figure 6A:
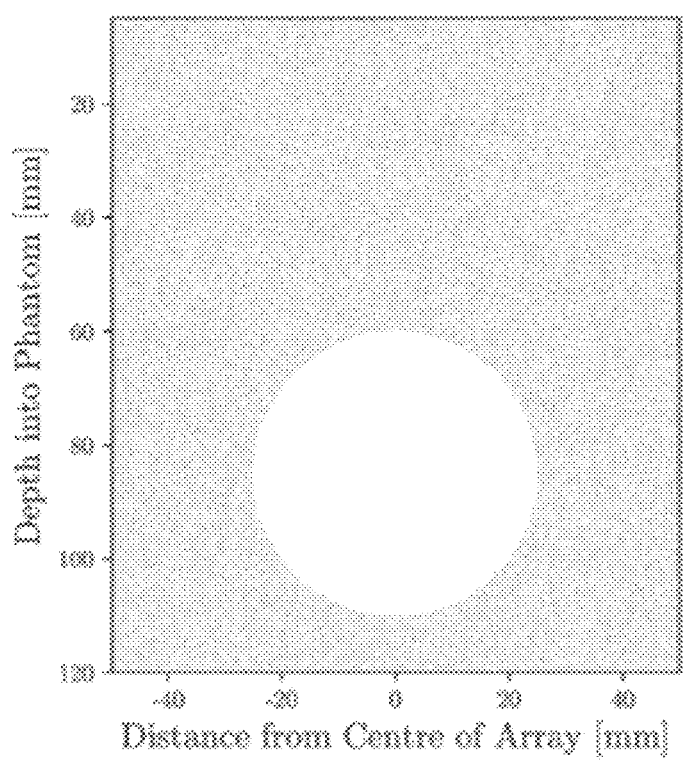
FIG. 6a depicts a Field II phantom designed to represent the CIRS tissue-mimicking phantom model 055.

All simulated data were generated using Field II software. The probe and phantoms were designed to model the experimental set-up as closely as possible. Five 1D arrays of transducer elements corresponding to the flexible array configurations recorded in Table I were created using the 'xdc rectangles' function with the same specifications as the one hundred twenty-eight (128) element flexible array from Olympus. The Field II phantom was designed to represent the CIRS' tissue-mimicking phantom model '055', shown in FIG. 6a, and was generated using six (6) scatterers per resolution cell to ensure a strong speckle response. The sampling frequency was set to fifty (50) MegaHertz (MHz). Using 'calc scat all' the full matrix of transmit-receive signals was recorded for each array shape. Since FIELD II is a fully linear system, these data can be reconstructed into the format of the channel data recorded by an experimental scanner for any arbitrary scan sequence without the need to re-run the simulator. These channel data corresponding to the user defined scan sequence were used as the input for the shape estimation algorithm. No apodization was applied to these signals during this reconstruction process.

The root mean square error (RMSE, Equation 3) of the estimated transducer element coordinate $\hat{p}$ to the actual element coordinate p is used to measure the accuracy of the shape estimation method according to embodiments of the present invention, i.e.

$$RMSE = \sqrt{\frac{1}{N}\sum_{i=1}^{N}(\hat{p}_i - p_i)^2} \tag{3}$$

wherein N equals one hundred twenty-eight (128), i.e. the number of transducer elements defining the one-dimensional flexible array of the demonstration flexible ultrasound device.

A series of shape metrics $S_j$ may be determined by executing a shape estimation method according to embodiments of the invention wherein a shape metric $S_j$ may be obtained for each assumed shape j of a predetermined series of assumed shapes of the flexible ultrasound device.

Figure 6B:
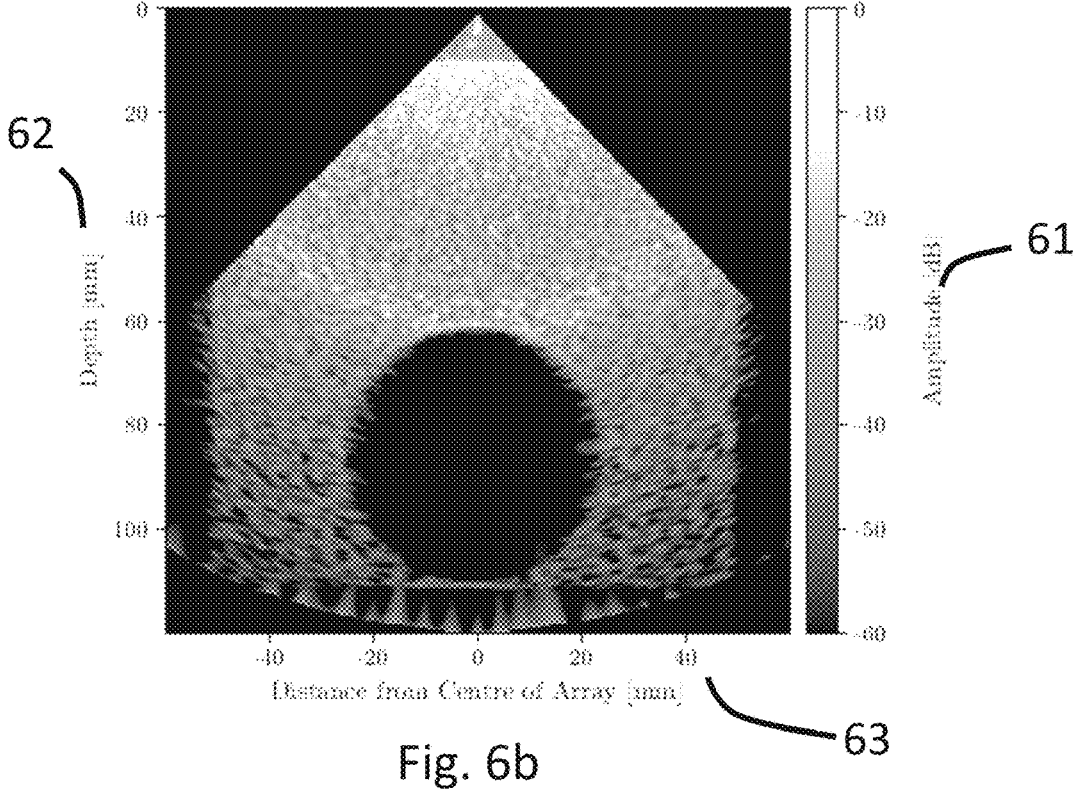
FIGS. 6b, 6c and 6d are bMode simulated images constructed from data recorded from three different shapes of a flexible array, wherein FIG. 6b corresponds with the correct shape of the flexible array, and FIG. 6c and FIG. 6d deviate from this shape.
Figures 6C, 6D:
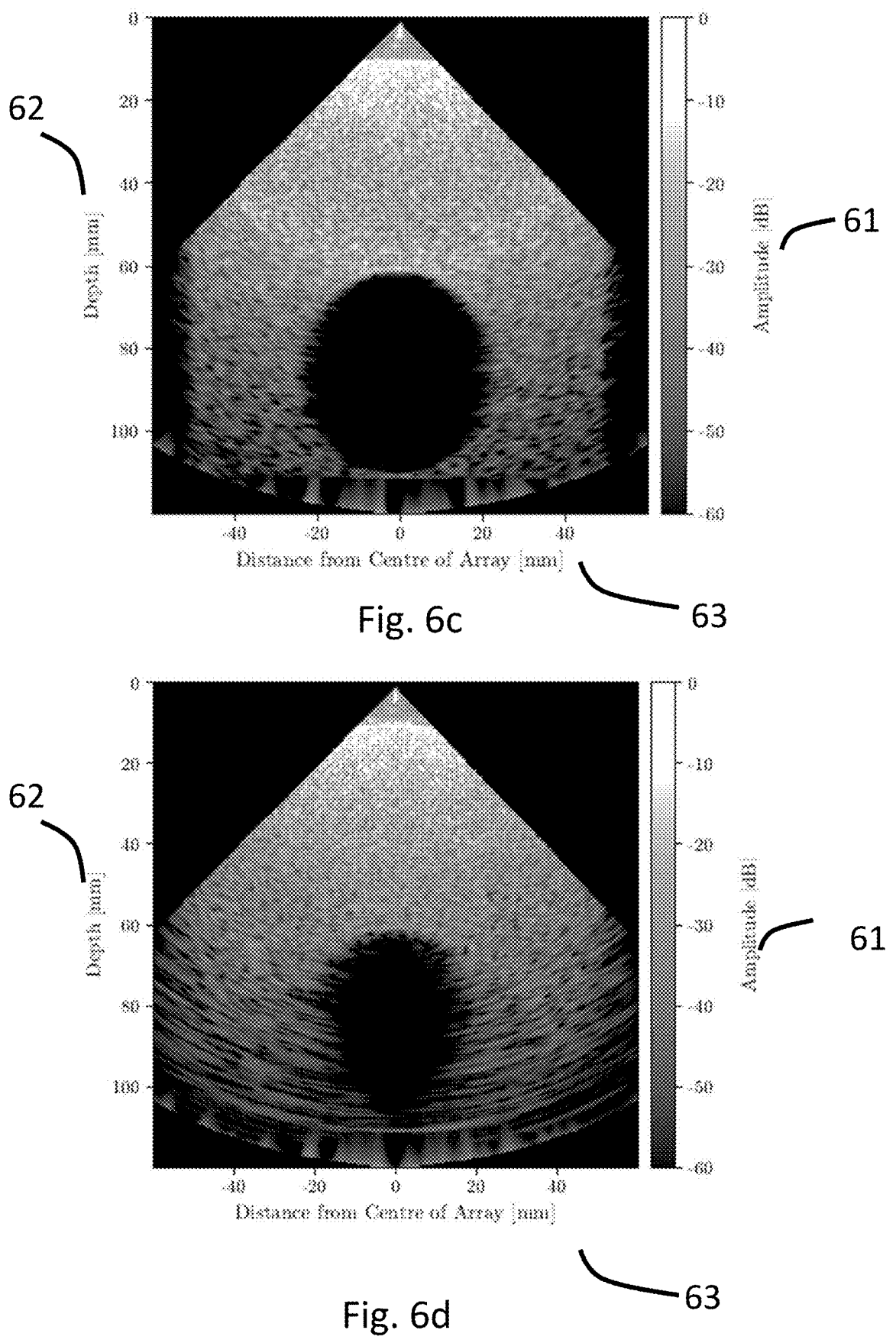

The uncertainty in testing the shape estimation method according to embodiments of the present invention may be dependent on the resolution between investigated shapes of the flexible ultrasound device, where increasing the shape resolution results in a decrease in the temporal resolution as more shapes must be investigated. The investigated shapes of the flexible ultrasound device were set linearly spaced between flat shape (i.e. θ=0°) and curved shape defining an opening angle θ equal to π/8, where the step size was determined with respect to the RMSE between adjacent shapes. Using a step size of opening angle θ equal to 0.04 radians or 2.5 degrees, the largest RMSE between any two steps is 28.5% of $$\lambda\left( = \frac{c}{f_0} \right),$$

so is much smaller than the wavelength. This step size corresponds to ten (10) different array shapes being passed to the shape estimation algorithm. The impact of the shape resolution is illustrated in FIGS. 6b, 6c and 6d, where simulated data generated from a known flat shaped ultrasound device were reconstructed with the correct array shape (i.e. opening angle θ=0.0°, FIG. 6b), at the first resolution step (i.e. θ=2.5°, FIG. 6c), and the final resolution step (i.e. θ=22.5°, FIG. 6d). In each of the images in FIGS. 6b, 6c and 6d, the amplitude value 61 (expressed in decibels, dB) per pixel is visualized as a grey-scale value, and the depth 62 (expressed in millimeters, mm) is plotted in function of the distance from the centre of the array 63 (expressed in millemeters, mm). Note that the same channel data have been used to generate each image of FIGS. 6b, 6c and 6d, but the transducer element locations in the beamformer have been modified corresponding to each array shape. As the RMSE of the transducer element array shape increases, the images become more defocused, thus highlighting the need to identify the actual shape of the flexible ultrasound device prior to image reconstruction.

To demonstrate the validity of the invention, the method according to embodiments of the present invention is first deployed under known flexible array shape conditions. This implies that the transmit delay times applied to the a first portion of the plurality of transducer elements in transmit mode correspond to the in-phase response while those in receive mode, i.e. when dealing with the echo signals, are iterated over a set of predetermined assumed shapes of the flexible ultrasound device (also referred to as assumed "array shapes"). In practice, this is equivalent to an autofocusing algorithm, whereby large quantities of redundant data must be recorded while only the data corresponding to correct array shape is retained.

The simulated Full Matrix Capture ('FMC') were beamformed into equivalent receive channel data of a single line transmit sequence. An opening angle θ of 90 degrees (°) with one transmit beam per degree and a focal depth (or transmit focus position) of 60 millimeters (mm) were deployed. The transmit delay times applied in transmit mode corresponded to the assumed shape of the flexible ultrasound device and the predetermined transmit focus position. These equivalent receive channel data were then processed further according to embodiments of the shape estimation method of the present invention in order to determine a shape metric for the assumed shape of the flexible ultrasound device, i.e. an echo signal phase variation across the respective receive channels was calculated by converting the received echo signal into a time delayed echo signal per respective receive channel and by quantifying, based on said time delayed echo signal, the echo signal phase variation of the received echo signal across the respective receive channels. The shape metric was then calculated based on the calculated echo signal phase variation across the respective receive channels for the assumed shape of the predetermined series of assumed shapes of the flexible ultrasound device and the predetermined transmit focus position.

According to test the technical advantage of specific embodiments of the present invention, a value of the shape metric $S_j$ was determined using the full depth axis from zero to 120 millimeters (mm) and twenty (20) focal depths per wavelength. The estimated values of the shape metric $S_j$ were then interpolated using a cubic spline, scaled from zero to one and recorded in FIG. 7. For display purposes the data have been inverted, so the peak maxima correspond to the predicted array shapes. The estimated actual shape of the flexible ultrasound device obtained by execution the shape estimation module according to embodiments of the present invention, is indicated with a star symbol in FIG. 7. The estimated actual shape is compared with the actual shape, indicated with a circle marker in FIG. 7, in function of the known or predefined array shape in transmit, expressed in function of the value of the opening angle θ on the Y-axis, and the inspected opening angle θ value in receive mode, on the X-axis.

Figure 7:
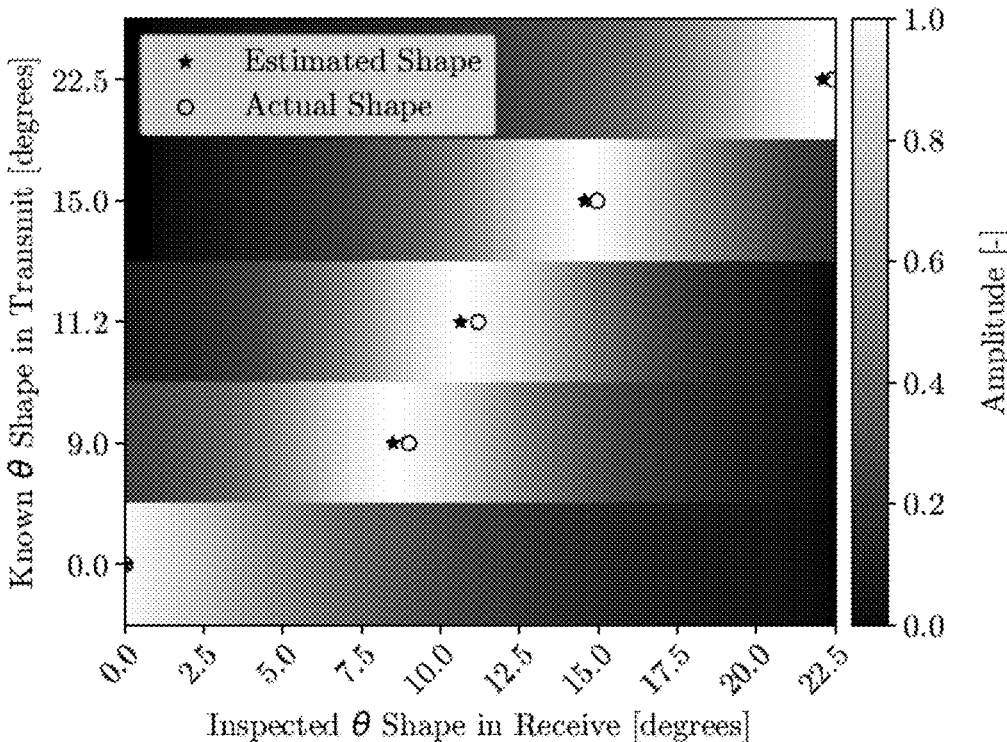
FIG. 7 illustrates a recorded view of the estimated values of the shape metric $S_j$ interpolated using a cubic spline, and scaled from zero to one.

Referring to FIG. 7, for each known shape of the flexible ultrasound device expressed on the Y-axis in function of the aforementioned opening angle θ, the estimated actual shape is closely matched to the (real) predefined actual shape. In the case of a flat shaped ultrasound device, i.e. a transducer element array configuration having an opening angle θ=0.0°, the actual shape of the flexible ultrasound device has been correctly estimated, whereas for non-flat or curved array shapes the estimated actual shape is always slightly underestimated.

The RMSE of the array element positions recorded in Table II show that the maximum RMSE is only 26.4 micrometers (μm) or 4.3% of λ, so is significantly less than the wavelength and shows the shape estimation algorithm is valid when applied to simulated data.

TABLE II

| Array shape | Simulated | | Experimental | |
|---|---|---|---|---|
| θ [degrees] | [μm] | [% λ] | [μm] | [% λ] |
| 0 | 0.0 | 0.0 | 0.0 | 0.0 |
| 9.0 | 19.4 | 3.1 | 36.4 | 5.9 |
| 11.3 | 19.0 | 3.1 | 33.7 | 5.4 |
| 15.0 | 26.4 | 4.3 | 14.7 | 2.4 |
| 22.5 | 20.5 | 3.3 | 0.0 | 0.0 |

Figure 8:
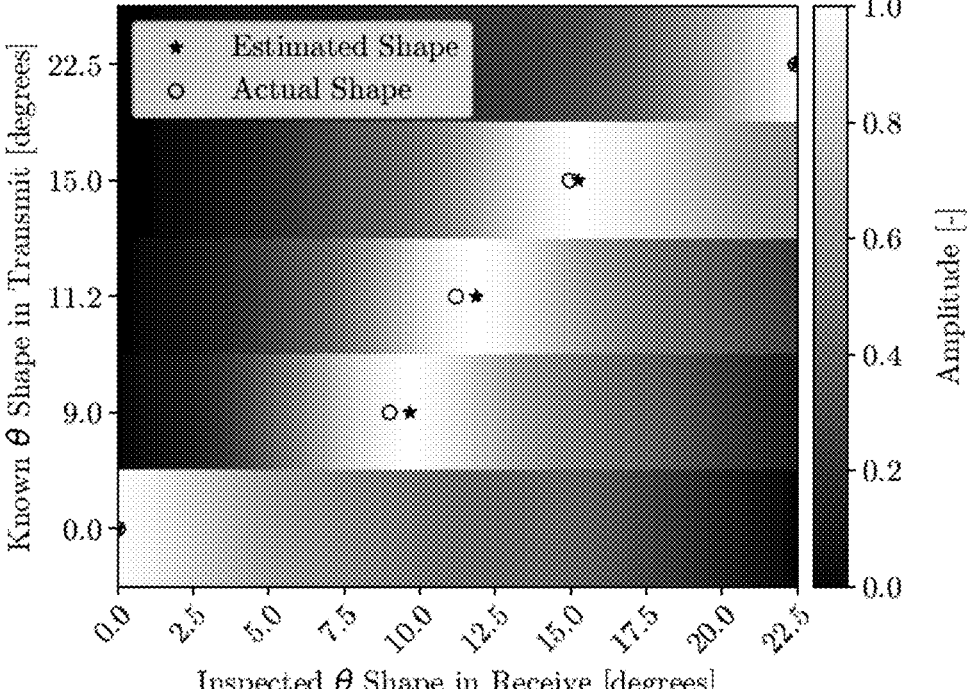
FIG. 8 depicts the time delays in transmit mode which calculated with respect to the known array shape and the recorded channel data processed under predetermined conditions.

These results were verified experimentally using the same scan sequence and using the aforementioned 3D-printed moulds to conform the flexible supporting platform on which the plurality of transducer elements are disposed during acquisition. The transmit delay times were calculated with respect to the known array shape and predetermined transmit focus position, and the recorded receive channel data were processed under the same conditions as above to calculate an echo signal phase variation across the respective receive channels. The results of these tests are shown in FIG. 8, indicating a close agreement with the simulated data. However, the experimental results consistently showed that the invention slightly overestimated the real actual shape. This discrepancy could be due to uncertainty in the design of the 3D-printed moulds but is still a very close prediction as demonstrated by the RMSE values in Table II. The RMSE of the experimentally acquired data are in the same order of magnitude as those from the simulated data, where the largest error was within 6% λ.

Figure 9:
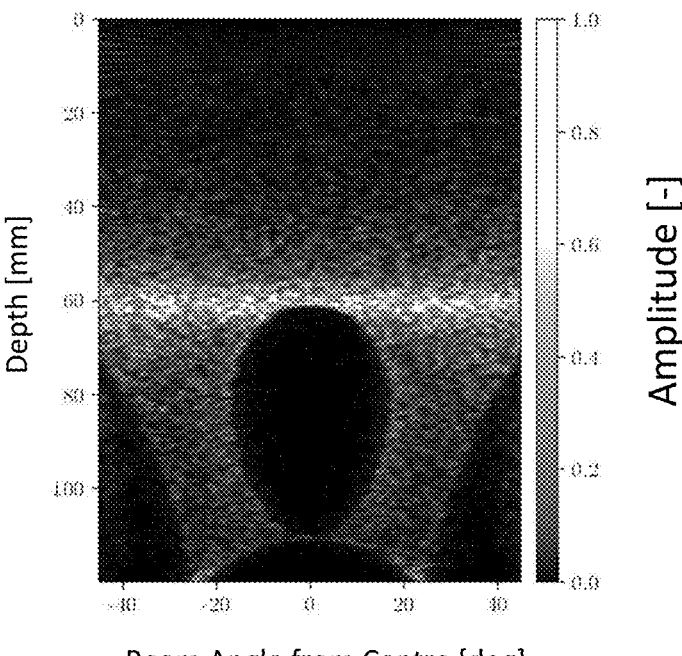
FIG. 9 shows a map of sign bit variance for flat transducer with correct delays applied in transmit mode, wherein the variance has been inverted for display purposes.

Referring to FIG. 9, a map is depicted of sign bit variance values ($\sigma^2$) for a flat shaped flexible ultrasound device, i.e. an ultrasound device comprising a plurality of transducer elements disposed in an array configuration on the flexible supporting platform wherein the opening angle θ equals zero degrees, having a transmit focus position at 60 millimeters (mm) with precisely defined transmit delay times to drive a first portion of the transducer elements in transmit mode before being accumulated to determine or define the shape metric S related to this assumed flat shape. The calculated echo signal phase variance across the respective receive channels has been inverted for display purposes. From FIG. 9 it may be understood that the value of a shape metric $S_j$ may contain spatially sensitive information and hence, information relating to the (actual) shape of the flexible ultrasound device. The outcome of these tests may indicate that only positions or locations close to the transmit focus positions, i.e. the bright region in FIG. 9, may strongly influence the determined shape metric $S_j$, hence the outcome of the actual shape estimation method. Consequently, embodiments of the present invention may not require the full depth axis to determine a shape metric $S_j$, which has the technical advantage of a significant reduction or saving of the number of computations required to derived a shape metric $S_j$, hence a series of shape metrics, and consequently the estimation of an actual shape of the flexible ultrasound transducer.

The simulated data were used to ultrasound imaging an object using an ultrasound imaging system according to embodiments of the present invention, with the same parameters as described before, except the depth axis which was set to ±λ/2 from the transmit focus position. The total number of computations required per assumed shape of the flexible ultrasound device, expressed as the product between the number of transmit beams (or lines) and transmit focus positions (or focal depth), was reduced from 90×3896 to 90×20. The determined series of shape metrics $S_j$ for ten assumed shapes of flexible ultrasound devices (hence, ten assumed shapes of transducer element arrays) were recorded before being interpolated with a cubic spline, scaled between zero and one and being inverted. These results are recorded in FIG. 10 and the corresponding RMSEs are recorded in Table III (cf. "Simulated"). The same process was repeated using the experimental data also with the depth axis limited to ±λ/2 either side of the transmit focal depth. The experimental results were recorded in FIG. 11 and the corresponding RMSEs in Table III (cf. "Experimental").

TABLE III

| Array Shape | Simulated | | Experimental | |
|---|---|---|---|---|
| θ [deg] | [μm] | [% λ] | [μm] | [% λ] |
| 0 | 0.0 | 0.0 | 0.0 | 0.0 |
| 9.0 | 34.0 | 5.5 | 4.7 | 0.8 |
| 11.3 | 36.6 | 5.9 | 19.1 | 3.1 |
| 15.0 | 23.5 | 3.8 | 0.0 | 0.0 |
| 22.5 | 20.5 | 3.3 | 0.0 | 0.0 |

Figure 10:
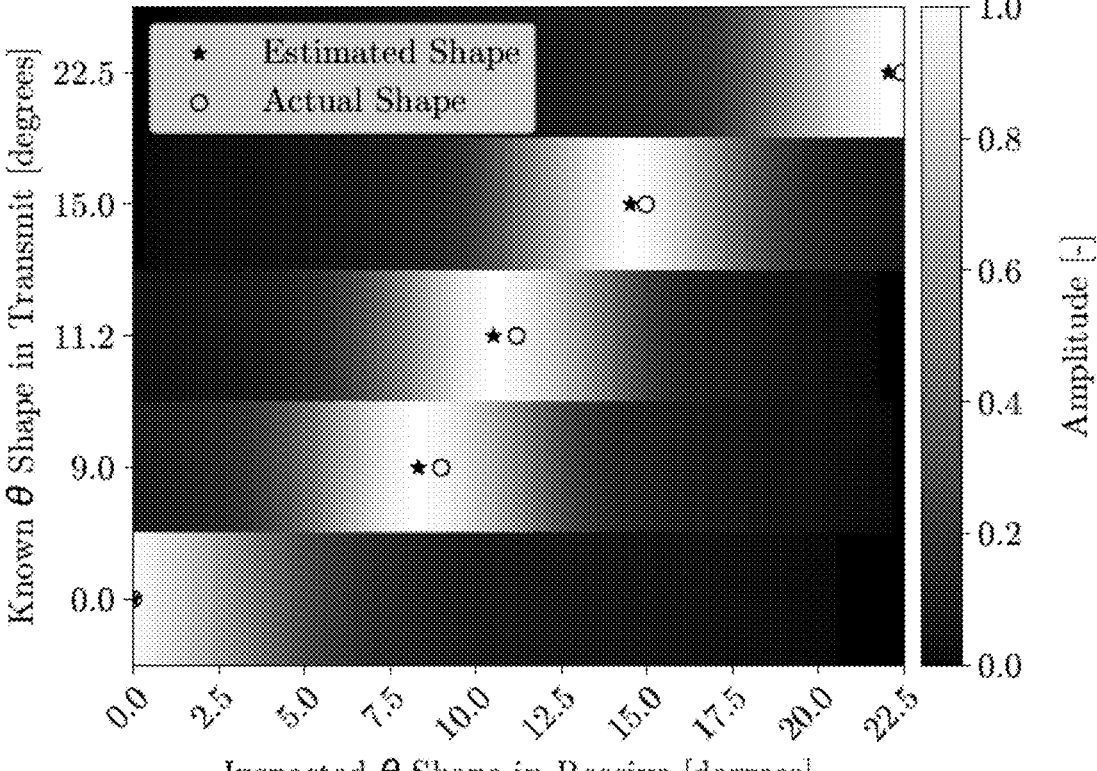
FIG. 10 depicts the values of the shape metric $S_j$ for all ten array shapes recorded before being interpolated with a cubic spline, scaled between zero and one and being inverted.

From FIG. 10 and FIG. 11 it may be observed that limiting the depth to that close to the transmit focus position may result in a sharper peak related to the real actual shape of the flexible ultrasound device. This means that the calculation of the echo signal variation, for example, by the variance, or another statistical parameter able to represent the phase variation across the receive channels of the flexible array, may be restricted to phase variation within the focus (or close to the focal point) for the determination of the shape metric $S_j$, and consequently the estimation of the actual shape of the flexible ultrasound device by selecting the smallest shape metric from the series of shape metrics. The maximum RMSE of array shape prediction was within 5.9% and 3.1% for the simulated and experimental results respectively, which are both less than when the full depth axis was inspected. This indicates that the actual shape estimation method according to embodiments of the present invention is indeed spatially sensitive, as further elaborated hereinafter.

As demonstrated above, when the assumed shape of the flexible ultrasound device and a transmit focus position are predetermined, the corresponding transmit delay times τ may be applied on a first portion of the plurality of transducer elements to transmit a transmit beam. Based on the received echo signal by a second portion of the transducer elements, an echo signal phase variation across the respective receive channels can be calculated to determine a shape metric $S_j$. Based on determined series of shape metrics, the actual shape of the flexible ultrasound device may be determined by selecting the optimal shape metric, corresponding with the smallest or largest shape metric—depending on how the shape metric is determined, of the determined series of shape metrics, wherein the assumed shape of the predetermined series of assumed shapes of the flexible ultrasound device corresponding to the optimal shape metric provides an estimation of the actual shape of the flexible ultrasound device. Hence, it is an advantage of the present invention to allow to estimate the actual shape of a flexible ultrasound device without any a priori information on the actual shape and in real-time.

Embodiments of the present invention may also comprise a step of calibrating the observed focused beam with respect to a predetermined assumed shape of the flexible ultrasound device. For this it is assumed that the flexibility of the ultrasound device, hence flexible supporting platform on which a plurality of transducer elements is disposed in an array configuration, is limited between flat shaped (opening angle θ=0°) and concave geometries (i.e. to fit or flex around at least a portion of the outer surface of a convexly shaped object) and it is symmetric about its apex. The phenomenon we aim to exploit is the offset of the beam focus resulting from the application of transmit delay times τ that do not correspond to the predetermined assumed shape of the flexible ultrasound device. This beam shift phenomenon is demonstrated in FIG. 12a and FIG. 12b using pressure fields simulated with Field II software. In both pressure fields the same transmit delay times have been applied to drive a first portion of the plurality of transducer elements, corresponding to a flat array focused at a 60 mm depth.

In FIG. 12a the flat array shape (indicated as white-grey dots at depth of 0 mm) has been simulated and in FIG. 12b the array shape corresponds to θ=π/8 (indicated as white-grey dots at depth of 0 mm). FIG. 12b illustrated the impact of using flat shaped transmit delay times to drive the same first portions of the plurality of transducer elements in transmit mode for a curved shaped device: a shift of the transmit focus closer to the transducer apex is noticeable. The extent of this beam shift is proportional to the shape of the array of transducer elements and so can be used to calibrate the actual shape estimation method and module.

The transmit delay times determined based on a flat shaped array were applied to every array shape in Table I. Using Field II, the pressure field was estimated at depths ranging from zero (0) to 120 mm with twenty (20) depths per wavelength. The depth of the absolute peak pressure relative to the set focus position at 60 mm, i.e. the beam shift, was recorded for each assumed array shape in FIG. 13. A second order polynomial was fitted to these measured data corresponding to the calibration curve used to estimate the expected location of the beam focus for a given array shape.

First the simulated FMC data were beamformed into the equivalent received channel data using the same scan sequence as before. However, the transmit time delays in transmit mode for all array shapes were identical and corresponded to those of a flat shaped flexible ultrasound device. The respective receive channel data were then passed to the shape estimation algorithm using the set of array shapes described in Table I. For each array shape investigated in receive mode, the expected depth of the focus was estimated using the beam shift calibration function as plotted in FIG. 13 and then depths ±λ/2 from this calibrated focus position were investigated. The results are shown in FIG. 14 and the corresponding RMSEs are given in Table IV. These simulated results show close agreement with the previous approaches and validate the use of a calibrated beam response to estimate the array shape. The maximum RMSE of array shape prediction for the simulated data was less than 8% λ which is still significantly less than the wavelength.

TABLE IV

| Array Shape | Simulated | | Experimental | |
|---|---|---|---|---|
| θ [deg] | [μm] | [% λ] | [μm] | [% λ] |
| 0 | 0.0 | 0.0 | 0.0 | 0.0 |
| 9.0 | 28.15 | 4.6 | 45.2 | 7.3 |
| 11.3 | 48.4 | 7.9 | 30.8 | 5.0 |
| 15.0 | 14.7 | 2.4 | 0.0 | 0.0 |
| 22.5 | 46.9 | 7.6 | 0.0 | 0.0 |

Next, experimental data were acquired using the same scan sequence and using the 3D-printed moulds to conform the flexible array during acquisition. The time delays in transmit mode for all array shapes were identical and corresponded to those of a flat array. The channel data were passed to the shape estimation algorithm which was executed on a Quadro P2000 GPU (NVIDIA, USA) as data processing means and the depths investigated were determined using the same calibration curve in FIG. 13 from the simulated analysis. The experimental shape estimation results from the calibrated analysis were recorded in FIG. 15 and the RMSEs in Table IV. The determined shape metrics were stored on the Quadro P2000 as data storage means. The experimental analysis shows that via calibration of the beam response a highly accurate measure of the array shape can be performed. Indeed, the RMSEs from the experimental data indicate that the shape accurately predicted in every case with a maximum RMSE within 8% λ. It is noted that the calibration may be used to select only one focal point for the shape prediction method, or may be used to select multiple focal points to be investigated.

An advantage of embodiments of the present invention is that the actual shape of a flexible ultrasound device may be estimated without the need of any spatial reference point and in real time with respect to ultrasound image reconstruction.

Indeed, by exploiting the echo signal phase variation within a set of received echo signals across the receive channels, wherein each receive channel is connected to a transducer element in receive mode, all the information or data from which the shape of the flexible array could be determined, is contained within the set of received signals. Therefore, the image target does not need to contain specific artefacts nor does the full image need to be generated for each array shape investigated. It is demonstrated that the array shape can be adequately parameterised with respect to the opening angle θ of a circular sector but it should be noted that other shape parameters could also be deployed. Once a shape parameter is determined, the position of the transducer elements or their respective coordinates may be derived depending on the applied array configuration.

The key variable underlying the accuracy of the algorithm is the speed of sound. The speed of sound does not necessarily need to be homogeneous; however, it should be well defined such that there is minimal uncertainty in the time-of-flight calculation of the element positions to each focus. Moreover, it is vital that the transmitted beam energy can be focused at a specific spatial position. This was verified by testing the algorithm using unfocused diverging waves that did not yield any positive results.

In terms of the array design, the degrees of freedom in the array shape estimation is set by the number of respective receive channels N. As the number of respective receive channels N increases, the accuracy in the echo signal phase variation calculation across the respective receive channels may increase but the range of potential array shapes also increases. It should also be noted that the element pitch of the array deployed here was $$\frac{\lambda}{1.5}$$

so its focusing capability was slightly compromised with respect to Nyquist spatial sampling. On the other hand, this is only likely to impact transmit beams at either extremity of the opening angle.

When offsetting the expected position of the focus using an aforementioned step of array shape calibration, the invention is constrained to a beam shift which may only occur along the axial dimension. Therefore, embodiments of the present invention were applied on array shapes that were symmetric about their apex. However, if only half of the array shape deviated from a flat shape and time delays corresponding to a completely flat array were applied, the beam offset would be characterized by both an axial and lateral shift. This phenomenon brings a secondary dimension to the array shape calibration process. Indeed, the calibration space could be extended to map a surface of beam shift values rather than just a line. In practice, this would require the sign bit variance to be computed at locations across the full image sector for each transmit event rather than just along the axial dimension. Increasing the number of receive foci for a given beam would facilitate shape estimation of non-symmetric array shapes but would compromise the temporal resolution of the system.

The temporal resolution has been paramount during the design of this invention for shape estimating a flexible transducer. There are two distinct aspects impacting the overall temporal resolution, namely the data acquisition rate and the shape estimation process. In terms of the workflow presented, the data acquisition rate depends on the number of transmit events and the depth of the transmit focus. It has been demonstrated that by calibrating the beam response to the array shape that a guess value is not required to initiate the array shape search. This means only a single acquisition sequence is required to find the correct shape. Without this calibration process a range of acquisition sequences, and therefore more transmit events, would be needed to find the correct array shape.

It has been shown that when the array shape is symmetric about its apex and is calibrated with respect to a flat array that the beam shift direction is always towards the apex. This means that the depth of the acquisition can be limited to half a wavelength beyond the transmit focus depth rather than the full image depth. This reduces the total data to be streamed per transmit event, decreasing the computational load with respect to the data streaming process used for image reconstruction. In practice, the transmit focus used for shape estimation could be moved closer to the array, further reducing the data streaming capacity required.

In both the simulated and experimental data presented, 90 transmit events or beams were used per acquisition. The spread in phase variance across the 90 beams was found to be very small, especially for beams in the centre of the image sector. This implies that fewer than 90 beams are required per acquisition to determine a representative estimate of the shape metric $S_j$. Therefore, the scan sequence used for array shape estimation does not need to mimic that used for image reconstruction and the number of transmit events used for shape estimation can be significantly reduced relative to that for image reconstruction.

The computational load of the overall shape estimation process depends on the number of array shapes investigated. In this article, 10 shapes between $\theta=0$ and $\pi/8$ radians were used, with an array shape resolution of 0.04 radians. This resolution has been shown to be sufficient here but is a key parameter to be set by the end-user. If fewer shapes are investigated then the computational load decreases and therefore the temporal resolution of the system increases.

For a given set of received signals, the temporal resolution depends on the number of array shapes, the number of transmit beams and the number of foci per beam investigated. Here, the number of computations required to find the estimated array shape was 10 array shapes×90 beams×20 foci=18,000 computations. Whereas to generate a single B-Mode image using the full depth axis from 0 to 120 mm corresponds to 3896 depths×times 90 beams=350,640 computations. Therefore, applying the array shape estimation algorithm, as it is presented in this article, requires only 5.2% of the computations needed to generate a B-mode image from the same scan sequence. This shows that the algorithm lends itself precisely to real-time array shape estimation.

Where in embodiments of the present invention reference is made to "shape metric" of a flexible array, reference may be made to a metric having a shape which depends on the number of different possible array shapes investigated in receive model. The number of different possible array shapes may be predetermined depending on the constraints of the design space set by a user of the invention. For example, in the detailed embodiments as described above, the shape of the metric S corresponds with [1×nShapes] matrix wherein nShapes equals the number of different array shapes and which was set to ten (10). The reader may understand that nShapes may be smaller or larger than ten (10). In addition, each of these ten (10) values represents the sum of the variances across a range of spatial points or the variance at a single point, as described above. In the figures showing the optimization across the different shapes, these ten (10) values have been interpolated using a cubic spline to smooth out the result so it becomes [1×200].

Although a GPU is described herein as data processing and storage means, the present invention is not limited thereto. For example, a computer comprising at least a processor and a memory may be used as the data processing and storage means, where the processor is the data processing means and the memory is the data storage means.

Where in embodiments of the present invention reference is made to "a shape metric of a flexible transducer array", reference may be made to a shape metric for estimating a shape of the flexible transducer array.

Where in embodiments of the present invention reference is made to a "a flexible substrate" or "flexible array", reference may be made to a re-shapeable platform adapted to bend or flex at least partly around an object following the curvature of the outer surface of the object, wherein the bending or flexing of the platform may result in a change of the shape of the platform between a substantially planar shape to a substantially convex shape.

Image reconstruction from the received channel data involves a reciprocal beamforming process to that used to focus the energy transmitted from the array. In receive mode the channel data are synthetically focused at depths axial to the direction of each transmitted beam, known as an image line. The parameters required to focus the energy in receive are identical to those in transmit meaning variation in the signal phase across the received signals is also sensitive to the shape of the array. By this definition of the beamforming process; variation in the signal phase across the receive aperture should be minimised at the focus and if uncertainty is introduced into the elements coordinates then the variation in the phase across the receive channels will increase. In light of this, we propose to measure this phase variation within a set beam space for a given array shape to determine a relative value describing its shape, according to embodiments of the present invention as described below.

The invention claimed is:

1. A method for estimating an actual shape of a flexible ultrasound device, wherein the flexible ultrasound device comprises a flexible supporting platform and a plurality of transducer elements disposed in an array configuration on the flexible supporting platform, the flexible supporting platform being a re-shapeable platform adapted to bend at least partly around an object following a curvature of an outer surface of the object, the method comprising:

a) determining a series of shape metrics based on a predetermined series of shapes of the flexible ultrasound device, wherein, for each shape of the predetermined series of shapes of the flexible ultrasound device, a corresponding shape metric is determined by executing the following steps:

a1) transmitting, based on a shape of the predetermined series of shapes of the flexible ultrasound device and on a first predetermined transmit focus position, a transmit beam focused on the first predetermined transmit focus position by driving a first portion of the plurality of transducer elements based on a transmit delay time;

a2) receiving, by a second portion of the plurality of transducer elements, an echo signal in response to the transmit beam, wherein each transducer element of the second portion of the plurality of transducer elements is electronically connected to a respective receive channel;

a3) calculating, in receive mode, an echo signal phase variation across the respective receive channels by converting the received echo signal into a time delayed echo signal per respective receive channel and quantifying, based on said time delayed echo signal, the echo signal phase variation of the received echo signal across the respective receive channels; and a4) determining a shape metric based on the calculated echo signal phase variation across the respective receive channels for the shape of the predetermined series of shapes of the flexible ultrasound device and the predetermined transmit focus position; and b) selecting an optimal shape metric corresponding with the smallest or largest shape metric of the determined series of shape metrics, wherein the shape of the predetermined series of shapes of the flexible ultrasound device corresponding to the optimal shape metric provides an estimation of the actual shape of the flexible ultrasound device.

2. The method according to claim 1, wherein steps a1), a2) and a3) are repeated for a second predetermined transmit focus position different from the first predetermined transmit focus position, and wherein the determined shape metric in step a4) is based on a weighted sum of the calculated echo signal phase variations across the respective receive channels for the shape of the predetermined series of shapes of the flexible ultrasound device and respectively the first and the second predetermined transmit focus position of the flexible ultrasound device.

3. The method according to claim 1, wherein the first and the second portion of the plurality of transducer elements are identical.

4. The method according to claim 1, wherein the step of quantifying the echo signal phase variation comprises a step of computing a statistical parameter, wherein the statistical parameter is selected from the group consisting of the variance, the covariance, the mean, the correlation, the standard deviation, or the skewness.

5. The method according to claim 1, further comprising a step of quantizing the time delayed echo signal per respective receive channel before quantifying the echo signal phase variation.

6. The method according to claim 5, wherein the quantizing step comprises the application of a binary phase descriptor on the time delayed echo signal phase $s_i$ per respective receive channel i at the $k^{th}$ depth, wherein the quantized echo signal phase $b_i$ is defined according to $$b_i = \begin{cases} +1 & \text{if } s_i(k) \geq 0, \\ -1 & \text{if } s_i(k) < 0 \end{cases} \text{ and } \sum b_i^2 = N,$$

wherein N equals the number of transducer elements of the second portion, wherein $1 \leq i \leq N$, and wherein k is between 1 and a predetermined number of depth points.

7. The method according to claim 1, wherein the plurality of transducer elements are arranged in n rows and m columns, wherein n+m≥3.

8. The method according to claim 1, wherein the step of selecting the optimal shape metric of the determined series of shape metrics further comprises a step of using a stochastic gradient descent.

9. An ultrasound imaging system, comprising:
a flexible ultrasound device, wherein the flexible ultrasound device comprises a flexible supporting platform and a plurality of transducer elements disposed in an array configuration on the flexible supporting platform, the flexible supporting platform being a re-shapeable platform adapted to bend at least partly around an object following a curvature of an outer surface of the object;
a data storage unit storing a shape estimation module and configured to store data from the shape estimation module; and
a data processing unit connected to the flexible ultrasound device and the data storage unit, and adapted to receive data from the flexible ultrasound device and to process the received data;
wherein, when executed, the shape estimation module performs the steps of:
a) determining a series of shape metrics based on a predetermined series of shapes of the flexible ultrasound device, wherein, for each shape of the predetermined series of shapes of the flexible ultrasound device, a corresponding shape metric is determined by executing the following steps:
a1) transmitting, based on a shape of the predetermined series of shapes of the flexible ultrasound device and on a first predetermined transmit focus position, a transmit beam focused on the first predetermined transmit focus position by driving a first portion of the plurality of transducer elements based on a transmit delay time;
a2) receiving, by a second portion of the plurality of transducer elements, an echo signal in response to the transmit beam, wherein each transducer element of the second portion of the plurality of transducer elements is electronically connected to a respective receive channel;
a3) calculating, in receive mode, an echo signal phase variation across the respective receive channels by converting the received echo signal into a time delayed echo signal per respective receive channel and quantifying, based on said time delayed echo signal, the echo signal phase variation of the received echo signal across the respective receive channels; and
a4) determining a shape metric based on the calculated echo signal phase variation across the respective receive channels for the shape of the predetermined series of shapes of the flexible ultrasound device and the predetermined transmit focus position; and
b) selecting an optimal shape metric corresponding with the smallest or largest shape metric of the determined series of shape metrics, wherein the shape of the predetermined series of shapes of the flexible ultrasound device corresponding to the optimal shape metric provides an estimation of the actual shape of the flexible ultrasound device.

10. The ultrasound imaging system according to claim 9, wherein steps a1), a2) and a3) when executing the shape estimation module, are repeated for a second predetermined transmit focus position different from the first predetermined transmit focus position, and
wherein the determined shape metric in step a4) is based on a weighted sum of the calculated echo signal phase variations across the respective receive channels for the shape of the predetermined series of shapes of the flexible ultrasound device and respectively the first and the second predetermined transmit focus position of the flexible ultrasound device.

11. The ultrasound imaging system according to claim 9, wherein the first and the second portion of the plurality of transducer elements are identical.

12. The ultrasound imaging system according to claim 9, wherein, when executing the shape estimation module, the step of quantifying the echo signal phase variation comprising a step of computing a statistical parameter,
wherein the statistical parameter is selected from the group consisting of the variance, the covariance, the mean, the correlation, the standard deviation, or the skewness.

13. The ultrasound imaging system according to claim 9, further comprising, when executing the shape estimation module, a step of quantizing the time delayed echo signal per respective receive channel before quantifying the echo signal phase variation.

14. The ultrasound imaging system according to claim 13, wherein, when executing the shape estimation module, the quantizing step comprising the application of a binary phase descriptor on the time delayed echo signal phase $s_i$ per respective receive channel i at the $k^{th}$ depth according to $$b_i = \begin{cases} +1 & \text{if } s_i(k) \geq 0, \\ -1 & \text{if } s_i(k) < 0 \end{cases} \text{ and } \sum b_i^2 = N,$$

wherein N equals the number of transducer elements of the second portion, wherein $1 \leq i \leq N$, and wherein k is between 1 and a predetermined number of depth points.

15. A computer program comprising instructions to cause the system according to claim 9 to execute the steps of a method for estimating an actual shape of a flexible ultrasound device, wherein the flexible ultrasound device comprises a flexible supporting platform and a plurality of transducer elements disposed in an array configuration on the flexible supporting platform, the flexible supporting platform being a re-shapeable platform adapted to bend at least partly around an object following a curvature of an outer surface of the object, the method comprising:

a) determining a series of shape metrics based on a predetermined series of shapes of the flexible ultrasound device, wherein, for each shape of the predetermined series of shapes of the flexible ultrasound device, a corresponding shape metric is determined by executing the following steps:

a1) transmitting, based on a shape of the predetermined series of shapes of the flexible ultrasound device and on a first predetermined transmit focus position, a transmit beam focused on the first predetermined transmit focus position by driving a first portion of the plurality of transducer elements based on a transmit delay time;

a2) receiving, by a second portion of the plurality of transducer elements, an echo signal in response to the transmit beam, wherein each transducer element of the second portion of the plurality of transducer elements is electronically connected to a respective receive channel;

a3) calculating, in receive mode, an echo signal phase variation across the respective receive channels by converting the received echo signal into a time delayed echo signal per respective receive channel and quantifying, based on said time delayed echo signal, the echo signal phase variation of the received echo signal across the respective receive channels; and a4) determining a shape metric based on the calculated echo signal phase variation across the respective receive channels for the shape of the predetermined series of shapes of the flexible ultrasound device and the predetermined transmit focus position; and b) selecting an optimal shape metric corresponding with the smallest or largest shape metric of the determined series of shape metrics, wherein the shape of the predetermined series of shapes of the flexible ultrasound device corresponding to the optimal shape metric provides an estimation of the actual shape of the flexible ultrasound device.

* * * * *